United States Patent
Boraiah et al.

(10) Patent No.: US 10,219,846 B2
(45) Date of Patent: Mar. 5, 2019

(54) INTERLOCKING INTRAMEDULLARY ROD ASSEMBLY FOR TREATING PROXIMAL TIBIAL FRACTURES

(71) Applicant: Nail Kinetics, LLC, Gulf Breeze, FL (US)

(72) Inventors: Sreevathsa Boraiah, Lake Grove, NY (US); Jan Paul Szatkowski, Gulf Breeze, FL (US)

( * ) Notice: Subject to any disclaimer, the term of this patent is extended or adjusted under 35 U.S.C. 154(b) by 0 days.

(21) Appl. No.: 15/061,639

(22) Filed: Mar. 4, 2016

(65) Prior Publication Data

US 2017/0252075 A1 Sep. 7, 2017

(51) Int. Cl.
| A61B 17/72 | (2006.01) |
| A61B 17/74 | (2006.01) |
| A61B 17/68 | (2006.01) |

(52) U.S. Cl.
CPC ........ *A61B 17/7241* (2013.01); *A61B 17/725* (2013.01); *A61B 17/7225* (2013.01); *A61B 17/74* (2013.01); *A61B 2017/681* (2013.01)

(58) Field of Classification Search
CPC ....................................... A61B 17/72–17/748
USPC ..................................................... 606/62–68
See application file for complete search history.

(56) References Cited

U.S. PATENT DOCUMENTS

| 7,824,419 | B2 | 11/2010 | Boraiah |
| 8,109,943 | B2 | 2/2012 | Boraiah et al. |
| 9,468,478 | B2 | 10/2016 | Boraiah |
| 9,757,169 | B2 | 9/2017 | Boraiah |
| 2002/0107578 | A1 | 8/2002 | Speitling et al. |
| 2007/0049940 | A1 | 3/2007 | Wallace et al. |
| 2007/0213757 | A1 | 9/2007 | Boraiah |
| 2007/0233103 | A1* | 10/2007 | Metzinger .............. A61B 17/72 606/62 |
| 2009/0048600 | A1 | 2/2009 | Matityahu et al. |
| 2010/0262166 | A1 | 10/2010 | Boraiah et al. |
| 2011/0066152 | A1* | 3/2011 | Keller .................. A61B 17/725 606/62 |
| 2011/0196370 | A1 | 8/2011 | Mikhail |
| 2012/0265202 | A1 | 10/2012 | Schwammberger et al. |
| 2014/0330274 | A1 | 11/2014 | Matityahu et al. |

OTHER PUBLICATIONS

Haidukewych et al., Reverse Obliquity Fractures of the Intertrochanteric Region of the Femur, The Journal of Bone and Joint Surgery, 2001, vol. 83-A, No. 5, pp. 643-650.
Kregor et al., Unstable Pertrochanteric Femoral Fractures, Journal of Orthopaedic Trauma, 2005, vol. 19, No. 1, pp. 63-66.

\* cited by examiner

*Primary Examiner* — Nicholas J Plionis
(74) *Attorney, Agent, or Firm* — Pandiscio & Pandiscio

(57) ABSTRACT

A novel interlocking intramedullary rod assembly which allows the surgeon to (i) secure a first bone fragment of a fractured bone (e.g., a distal bone fragment) to the interlocking intramedullary rod assembly in a fixed position, (ii) secure a second bone fragment of the fractured bone (e.g., a proximal bone fragment) to the interlocking intramedullary rod assembly in an adjustable manner, and (iii) thereafter selectively pivot the second bone fragment (e.g., the proximal bone fragment) relative to the first bone fragment (e.g., the distal bone fragment) so as to secure the two bone fragments in position relative to one another with the desired orientation.

18 Claims, 24 Drawing Sheets

INTERLOCKING INTRAMEDULLARY ROD ASSEMBLY FOR TREATING PROXIMAL TIBIAL FRACTURES

FIELD OF THE INVENTION

This invention relates generally to an interlocking intramedullary rod assembly for treating fractures of a long bone, and more particularly to an interlocking intramedullary rod assembly for treating fractures of the tibia.

BACKGROUND OF THE INVENTION

Fractures of the tibia are traditionally treated with either (i) an intramedullary rod (sometimes referred to as an intramedullary nail) which is positioned in the intramedullary canal of the tibia, or (ii) a plate applied to the side of the tibia and fixed in place with screws set into the tibia. The choice of using an intramedullary rod or a plate is generally based on the location and complexity of the fracture.

As noted above, the intramedullary rod is placed in the intramedullary canal of the tibia and typically provides excellent mechanical stability for the bone. Among other things, the intramedullary rod exhibits good weight-sharing properties. However, the use of an intramedullary rod also involves a more complex surgical procedure and higher cost.

Plates are generally simpler to deploy and less expensive than intramedullary rods. However, it can sometimes be difficult to achieve proper support for the fracture site with plates upon the application of weight.

Intramedullary rods have evolved over time.

The first generation of intramedullary rods essentially involved inserting a solid rod down the intramedullary canal of the bone. This type of intramedullary rod is relatively primitive and only grossly re-aligns the bone. The first generation of intramedullary rods does not control motion at the fracture line in any specific plane.

The second generation of intramedullary rods saw the introduction of the so-called interlocking intramedullary rod. The interlocking intramedullary rod allows for compression of the bone at the fracture site by allowing axial compression of the fracture. This axial compression of the fracture is achieved through the use of lag screws which pass through the bone (e.g., in the medial-to-lateral direction, posterior-to-anterior direction, etc.), across the intramedullary rod and back into the bone.

However, with current interlocking intramedullary rods, the surgeon cannot easily adjust the disposition of one of the bone fragments (e.g., the proximal bone fragment) relative to the other of the bone fragments (e.g., the distal bone fragment). This makes it challenging for the surgeon to align the two bone fragments relative to one another in an optimal manner. More particularly, with current interlocking intramedullary rods, the surgeon must first adjust the disposition of one of the bone fragments (e.g., the proximal bone fragment) relative to the other of the bone fragments (e.g., the distal bone fragment), then temporarily hold the two bone fragments in the desired alignment while the interlocking intramedullary rod is inserted into the intramedullary canal, and finally insert one or more lag screws through each of the bone fragments and through the interlocking intramedullary rod so as to secure the bone fragments to the interlocking intramedullary rod. As this occurs, one of the bone fragments may become misaligned relative to the other of the bone fragments, so that it is secured to the interlocking intramedullary rod in a non-optimal manner.

In view of the foregoing, it is an object of the present invention to provide a novel interlocking intramedullary rod assembly which allows the surgeon to (i) secure a first bone fragment of a fractured bone (e.g., a distal bone fragment) to the interlocking intramedullary rod assembly in a fixed position, (ii) secure a second bone fragment of the fractured bone (e.g., a proximal bone fragment) to the interlocking intramedullary rod assembly in an adjustable manner, and (iii) thereafter selectively pivot the second bone fragment (e.g., the proximal bone fragment) relative to the first bone fragment (e.g., the distal bone fragment) so as to secure the two bone fragments in position relative to one another with the desired orientation and/or with the desired degree of compression.

SUMMARY OF THE INVENTION

The present invention comprises the provision and use of a novel interlocking intramedullary rod assembly which allows the surgeon to (i) secure a first bone fragment of a fractured bone (e.g., a distal bone fragment) to the interlocking intramedullary rod assembly in a fixed position, (ii) secure a second bone fragment of the fractured bone (e.g., a proximal bone fragment) to the interlocking intramedullary rod assembly in an adjustable manner, and (iii) thereafter selectively pivot the second bone fragment (e.g., the proximal bone fragment) relative to the first bone fragment (e.g., the distal bone fragment) so as to secure the two bone fragments in position relative to one another with the desired orientation and/or with the desired degree of compression.

In one preferred form of the present invention, there is provided an interlocking intramedullary rod assembly for treating a fracture of a bone, said interlocking intramedullary rod assembly comprising:

an intramedullary rod comprising a distal section, a proximal section, and a lumen opening on said proximal section;

a pivoting component pivotally disposed in said lumen of said intramedullary rod, said pivoting component being selectively pivotable relative to the longitudinal axis of said intramedullary rod;

an adjustment screw disposed in said proximal section of said intramedullary rod;

a distal interlocking screw comprising a distal end and a proximal end; and a proximal interlocking screw comprising a distal end and a proximal end;

wherein said distal section of said intramedullary rod comprises a static distal seat for receiving said distal interlocking screw, and said proximal section of said intramedullary rod comprises a dynamic proximal seat for receiving said proximal interlocking screw;

wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod and to said pivoting component such that said proximal interlocking screw can be selectively pivoted relative to the longitudinal axis of said intramedullary rod by selectively pivoting said pivoting component; and wherein rotation of said adjustment screw causes said pivoting component to pivot relative to the longitudinal axis of said intramedullary rod, whereby to selectively pivot said proximal interlocking screw relative to the longitudinal axis of said intramedullary rod.

In another preferred form of the present invention, there is provided a method for treating a fracture in a bone, said method comprising:

providing an interlocking intramedullary rod assembly comprising:
an intramedullary rod comprising a distal section, a proximal section, and a lumen opening on said proximal section;
a pivoting component pivotally disposed in said lumen of said intramedullary rod, said pivoting component being selectively pivotable relative to the longitudinal axis of said intramedullary rod;
an adjustment screw disposed in said proximal section of said intramedullary rod;
a distal interlocking screw comprising a distal end and a proximal end; and
a proximal interlocking screw comprising a distal end and a proximal end;
wherein said distal section of said intramedullary rod comprises a static distal seat for receiving said distal interlocking screw, and said proximal section of said intramedullary rod comprises a dynamic proximal seat for receiving said proximal interlocking screw;
wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod and to said pivoting component such that said proximal interlocking screw can be selectively pivoted relative to the longitudinal axis of said intramedullary rod by selectively pivoting said pivoting component; and
wherein rotation of said adjustment screw causes said pivoting component to pivot relative to the longitudinal axis of said intramedullary rod, whereby to selectively pivot said proximal interlocking screw relative to the longitudinal axis of said intramedullary rod;

positioning said intramedullary rod in the intramedullary canal of the bone so that said distal section of said intramedullary rod resides within the shaft of the bone and said proximal section of said intramedullary rod resides within a proximal portion of the bone;

inserting said distal interlocking screw through the bone, through said static distal seat and back into the bone, and inserting said proximal interlocking screw through the proximal portion of the bone, through said dynamic proximal seat and back into the proximal portion of the bone; and adjusting the disposition of said adjustment screw within the lumen of said intramedullary rod so as to pivot the proximal portion of the bone relative to the remainder of the bone, whereby to secure the proximal portion of the bone in position relative to the remainder of the bone with the desired orientation and/or with the desired degree of compression.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel interlocking intramedullary rod assembly which allows the surgeon to (i) secure a first bone fragment of a fractured bone (e.g., a distal bone fragment) to the interlocking intramedullary rod assembly in a fixed position, (ii) secure a second bone fragment of the fractured bone (e.g., a proximal bone fragment) to the interlocking intramedullary rod assembly in an adjustable manner, and (iii) thereafter selectively pivot the second bone fragment (e.g., the proximal bone fragment) relative to the first bone fragment (e.g., the distal bone fragment) so as to secure the two bone fragments in position relative to one another with the desired orientation and/or with the desired degree of compression.

Novel Interlocking Intramedullary Rod Assembly

Figure 1:
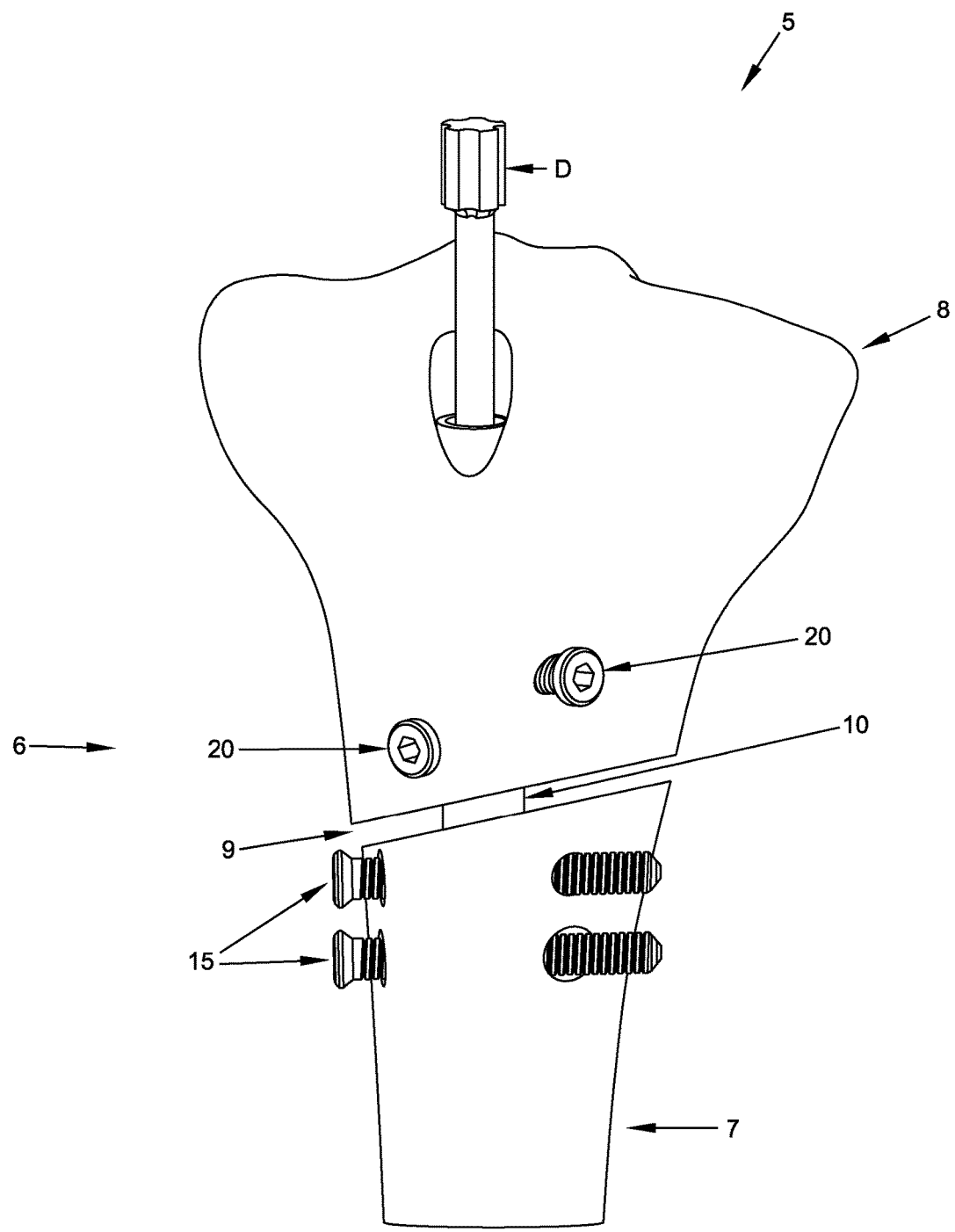
FIG. 1 is a schematic view showing a novel interlocking intramedullary rod assembly formed in accordance with the present invention, with the novel interlocking intramedullary rod assembly being disposed in a fractured tibia, and with the interlocking intramedullary rod assembly and the fractured tibia being shown prior to partial reduction of the fracture.
Figure 2:
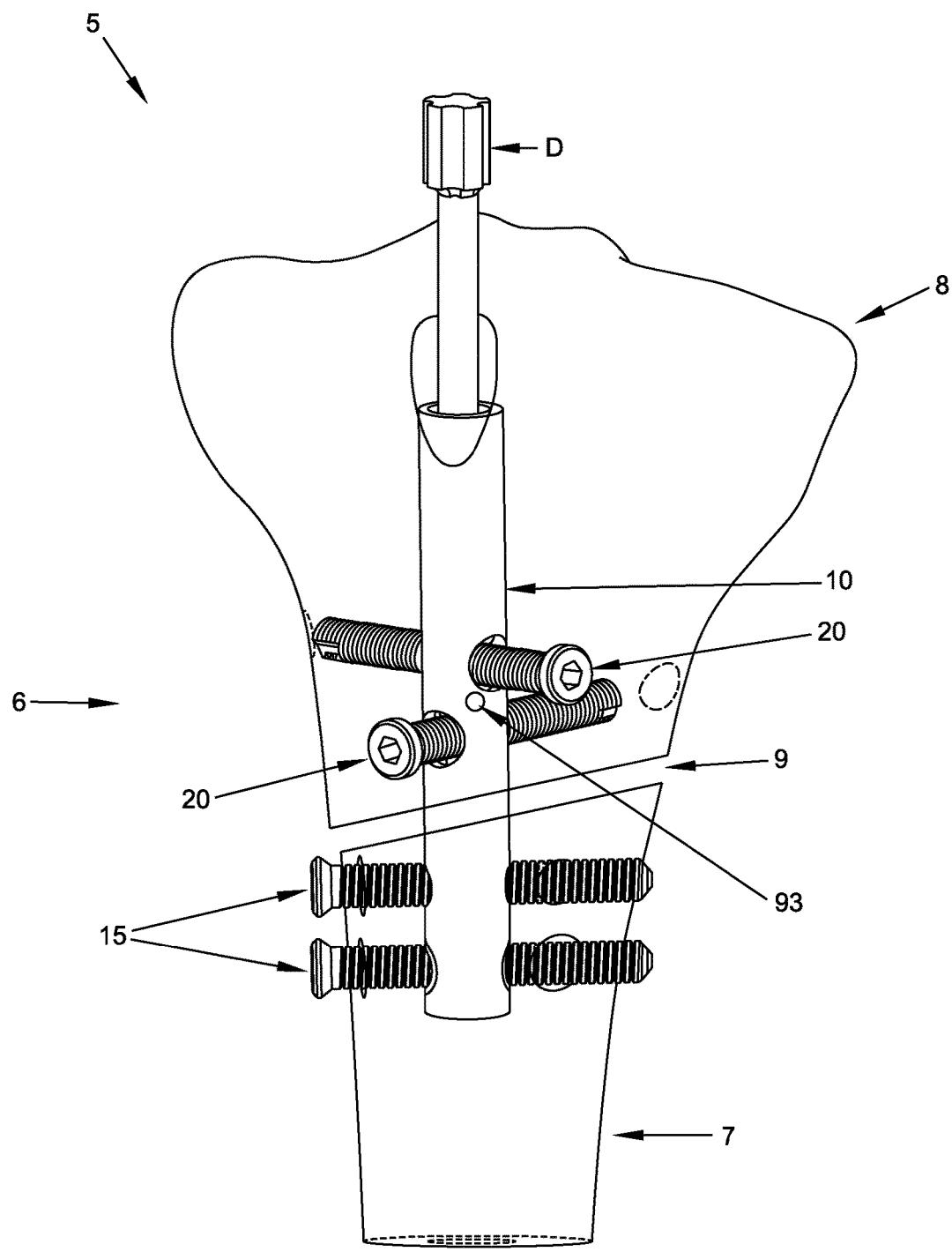
FIGS. 2-5 are schematic views showing further details of the novel interlocking intramedullary rod assembly of FIG. 1.
Figure 3:
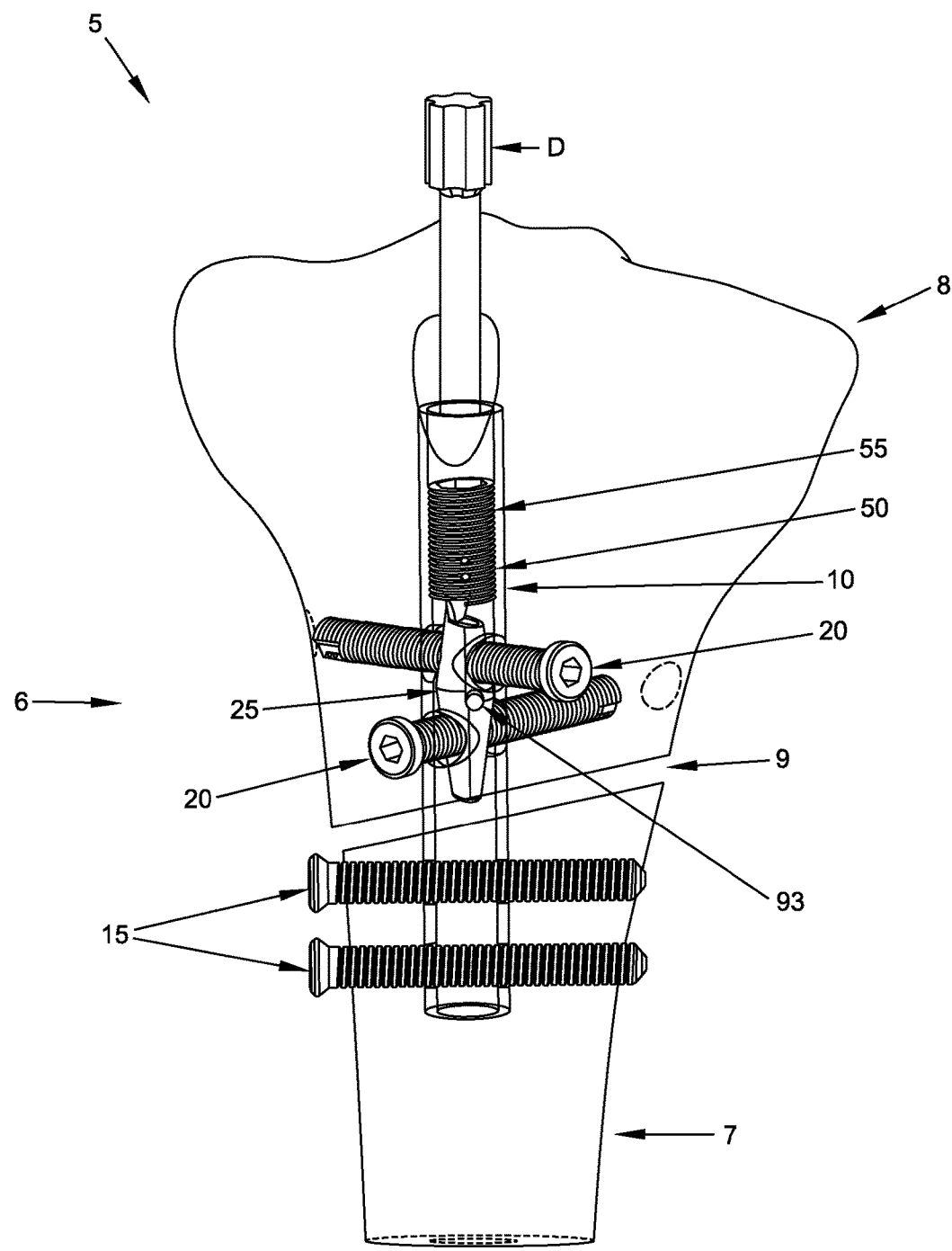

Looking first at FIGS. 1-3, there is shown a novel interlocking intramedullary rod assembly 5 formed in accordance with the present invention. Novel interlocking intramedullary rod assembly 5 may be used to secure two bone fragments of a tibia 6 (e.g., a distal bone fragment 7 and a proximal bone fragment 8) across a fracture line 9. Novel interlocking intramedullary rod assembly 5 generally comprises an intramedullary rod 10, one or more distal interlocking screws 15, one or more proximal interlocking screws 20, and a pivoting component 25 pivotally mounted within intramedullary rod 10 for engagement by one or more proximal interlocking screws 20, as will hereinafter be discussed in greater detail.

Figure 4:
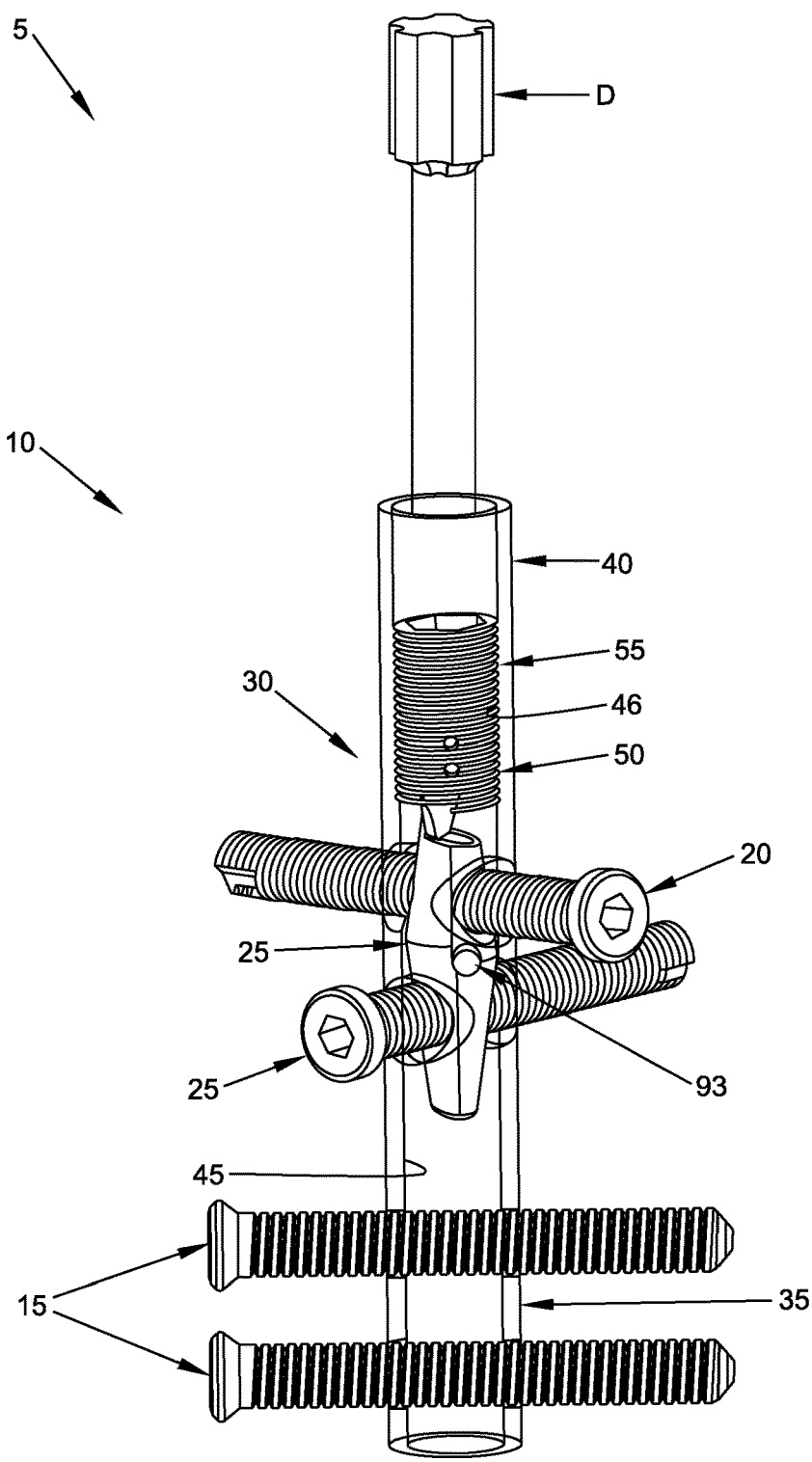
Figure 5:
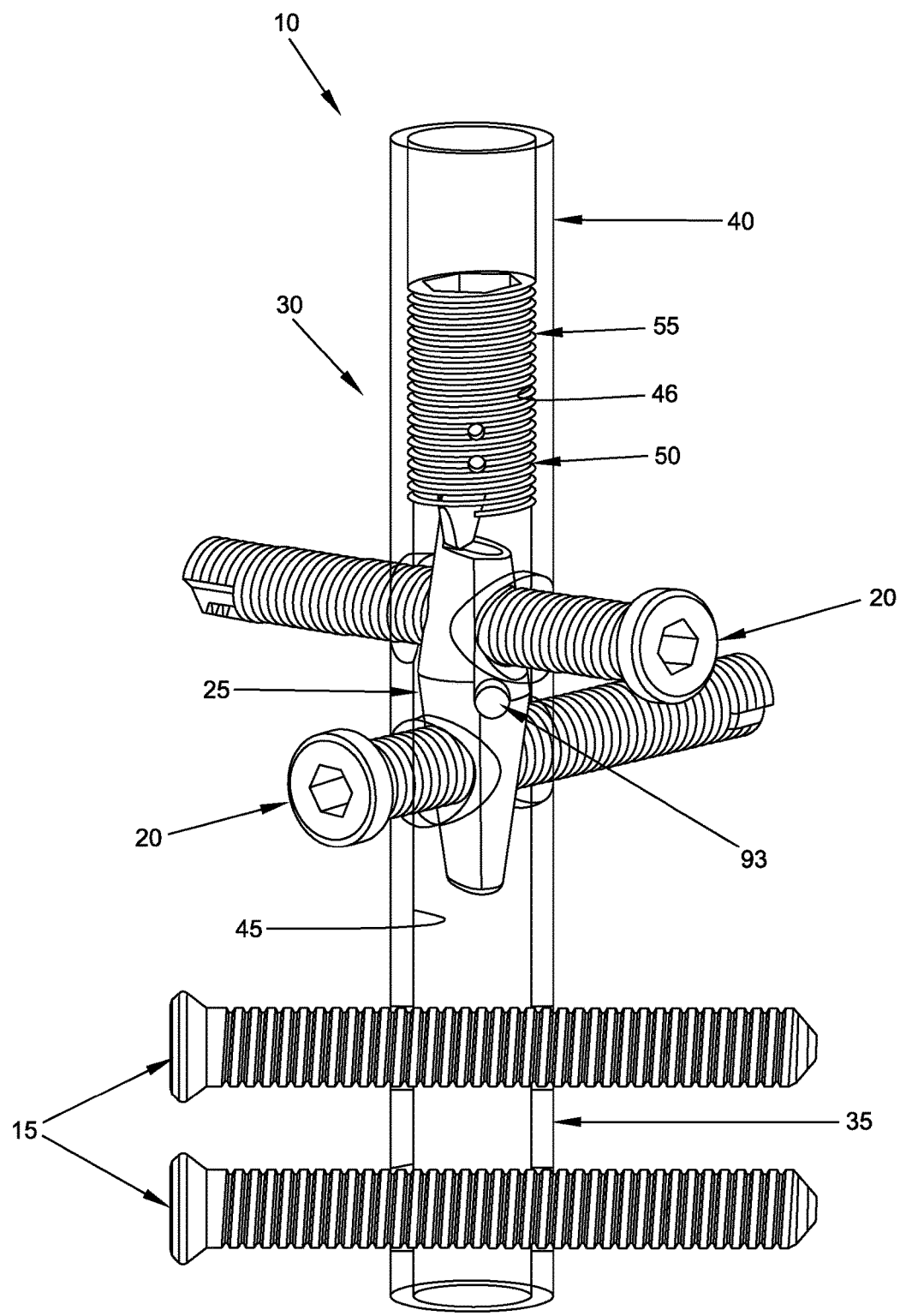
Figure 6:
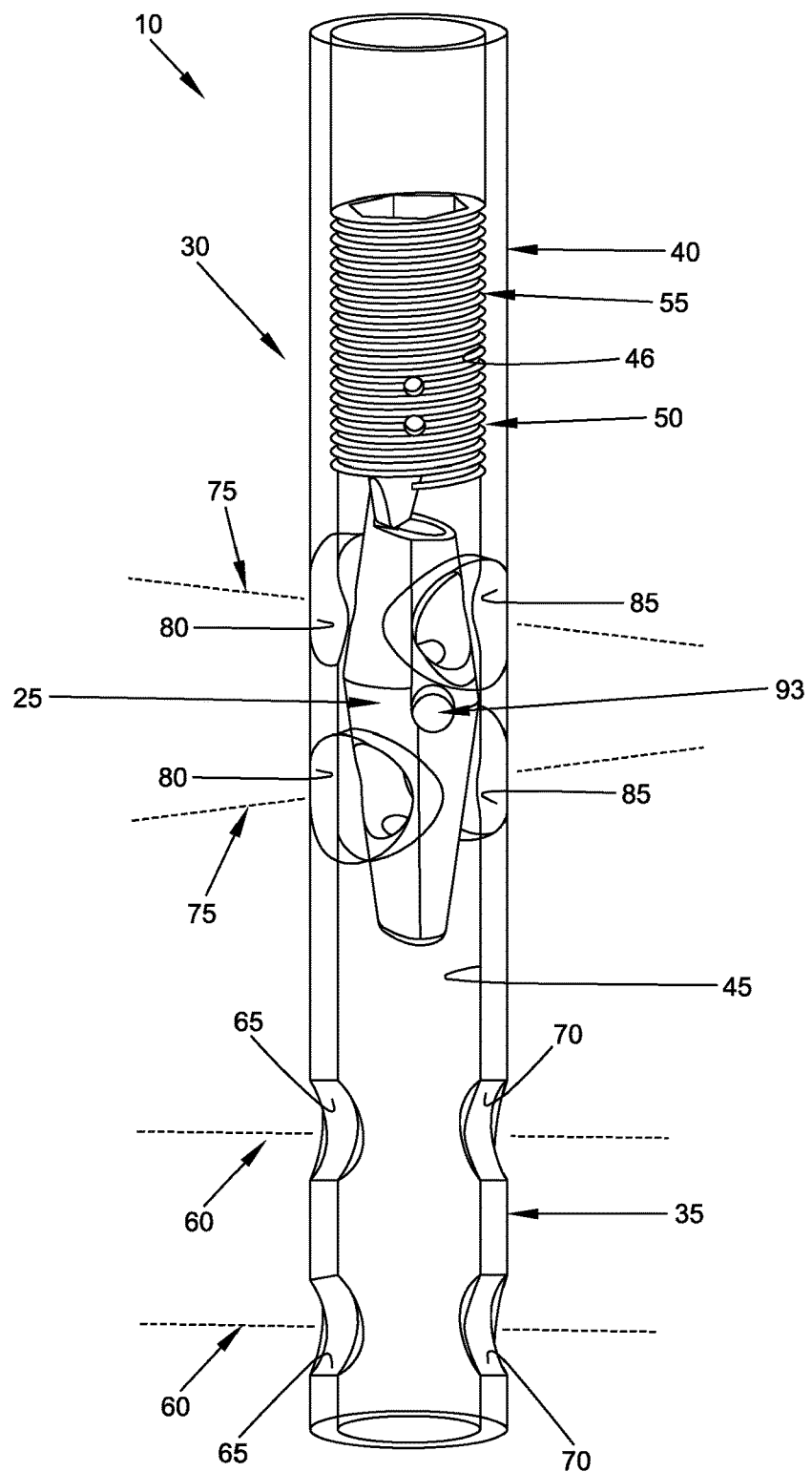
FIG. 6 is a schematic view showing a pivoting component, an adjustment screw and a set screw of the novel interlocking intramedullary rod assembly of FIG. 1, with the pivoting component being pivotally disposed within a tube of the novel interlocking intramedullary rod assembly.
Figure 7:
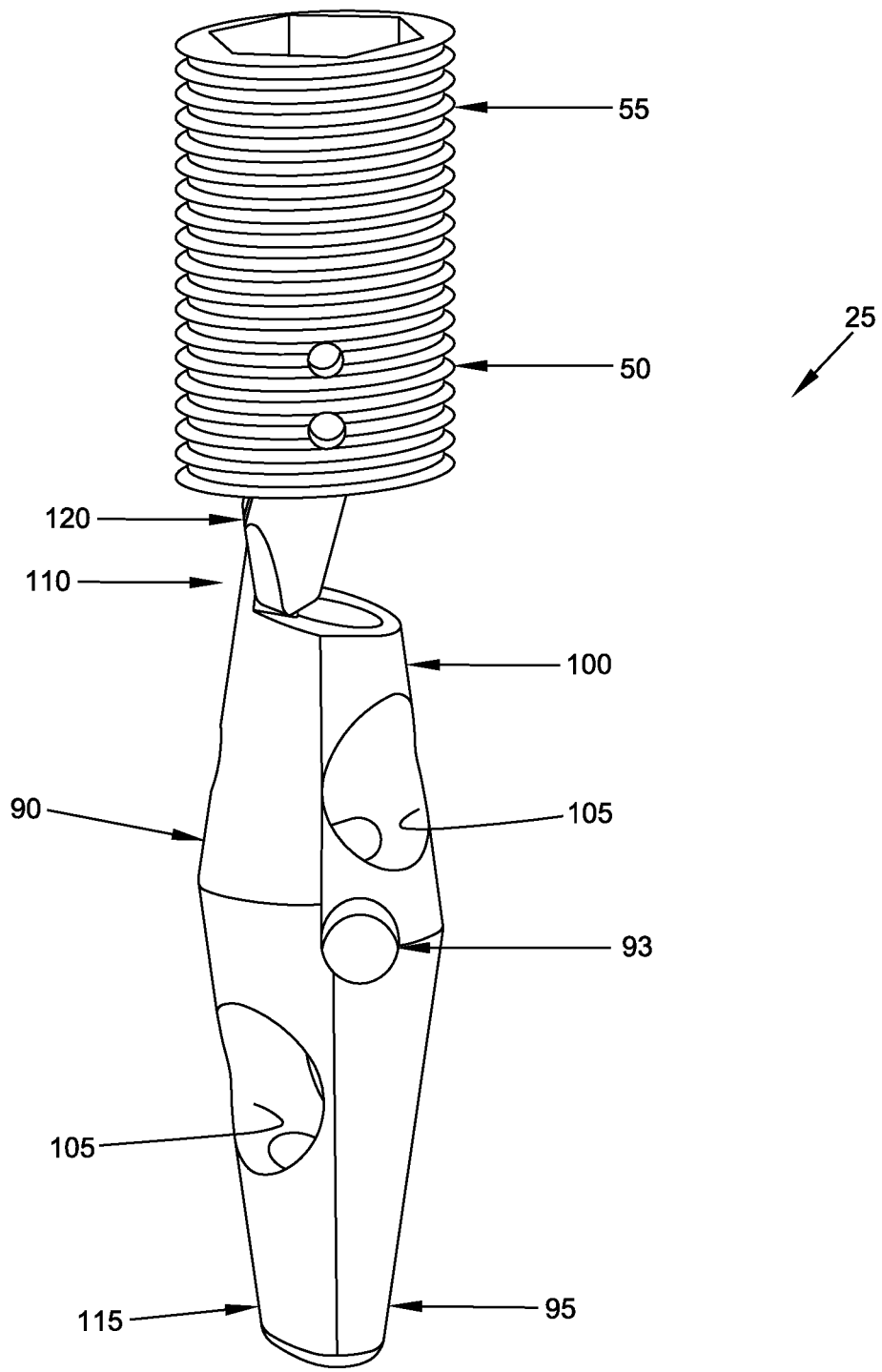
FIGS. 7-11 are schematic views showing further details of the pivoting component, adjustment screw and set screw of FIG. 6.
Figure 8:
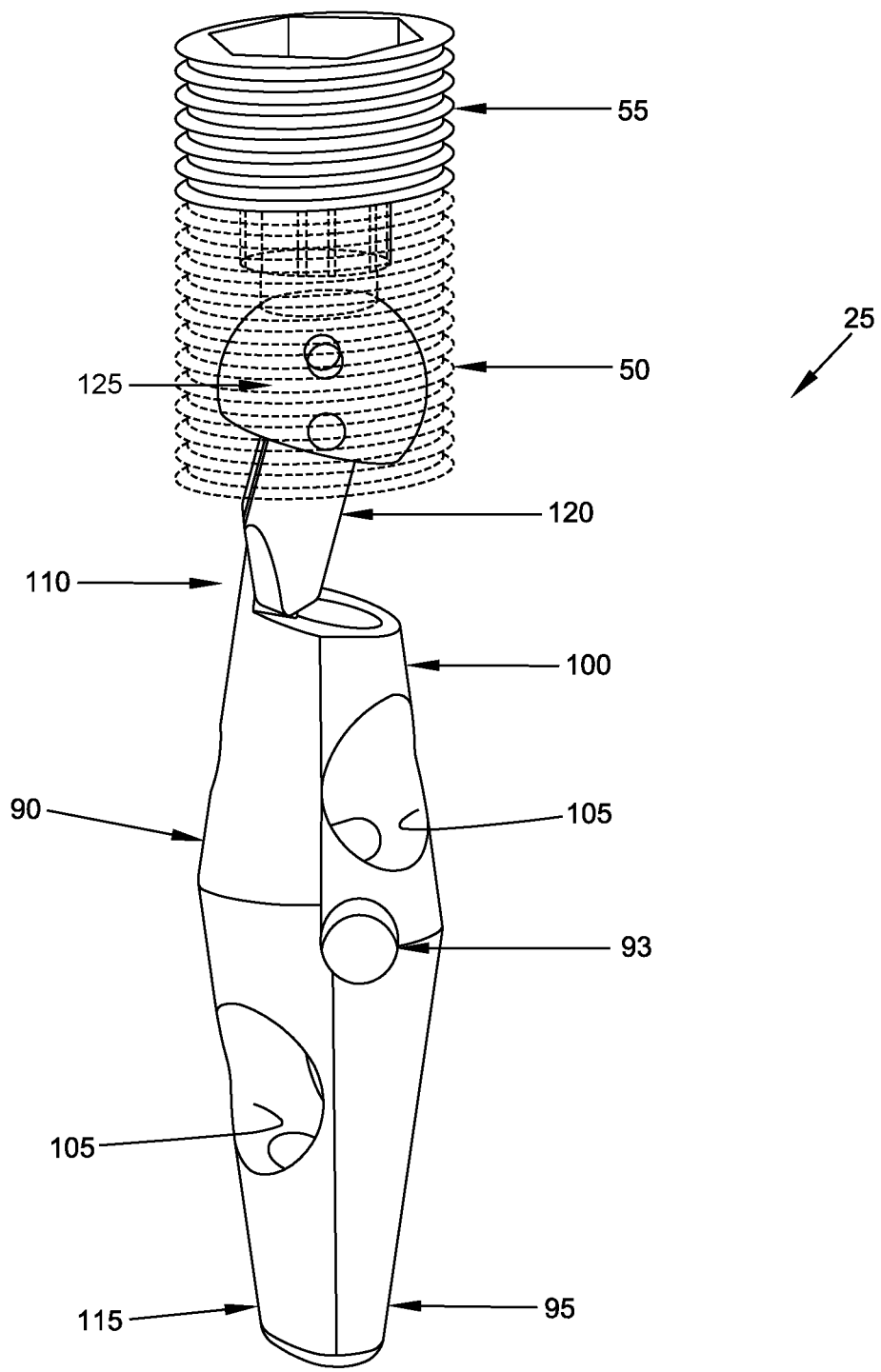
Figure 9:
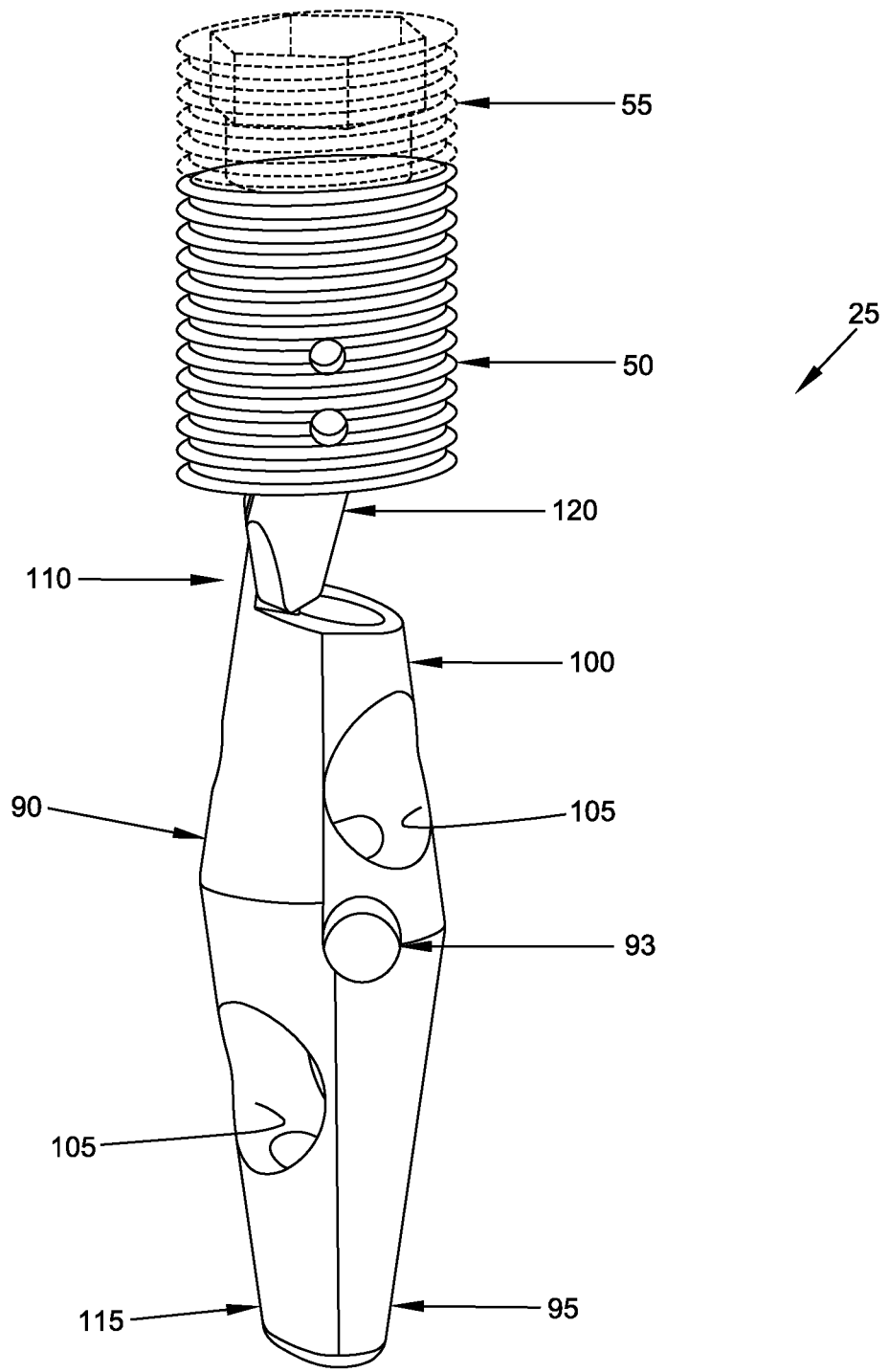
Figure 10:
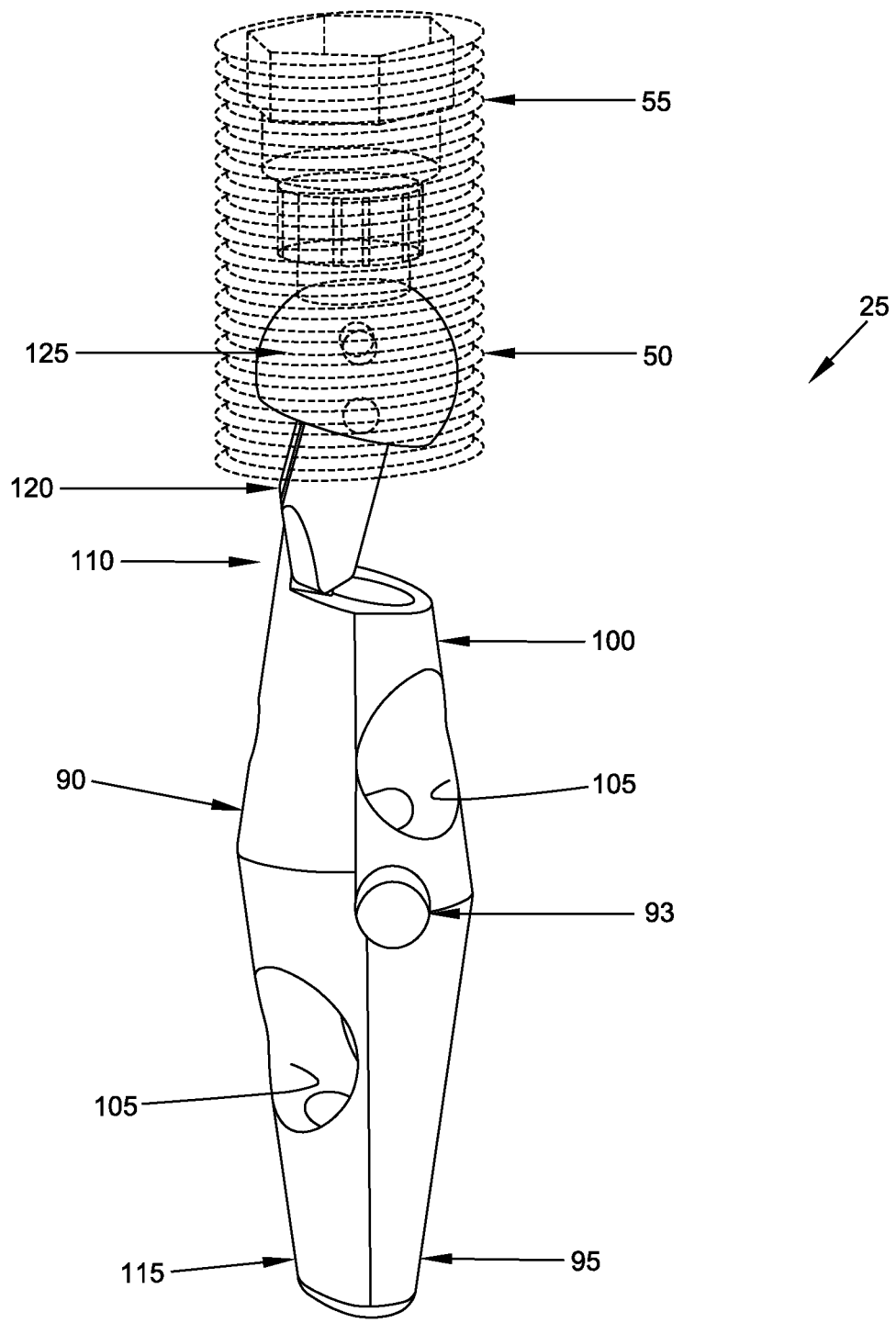
Figure 11:
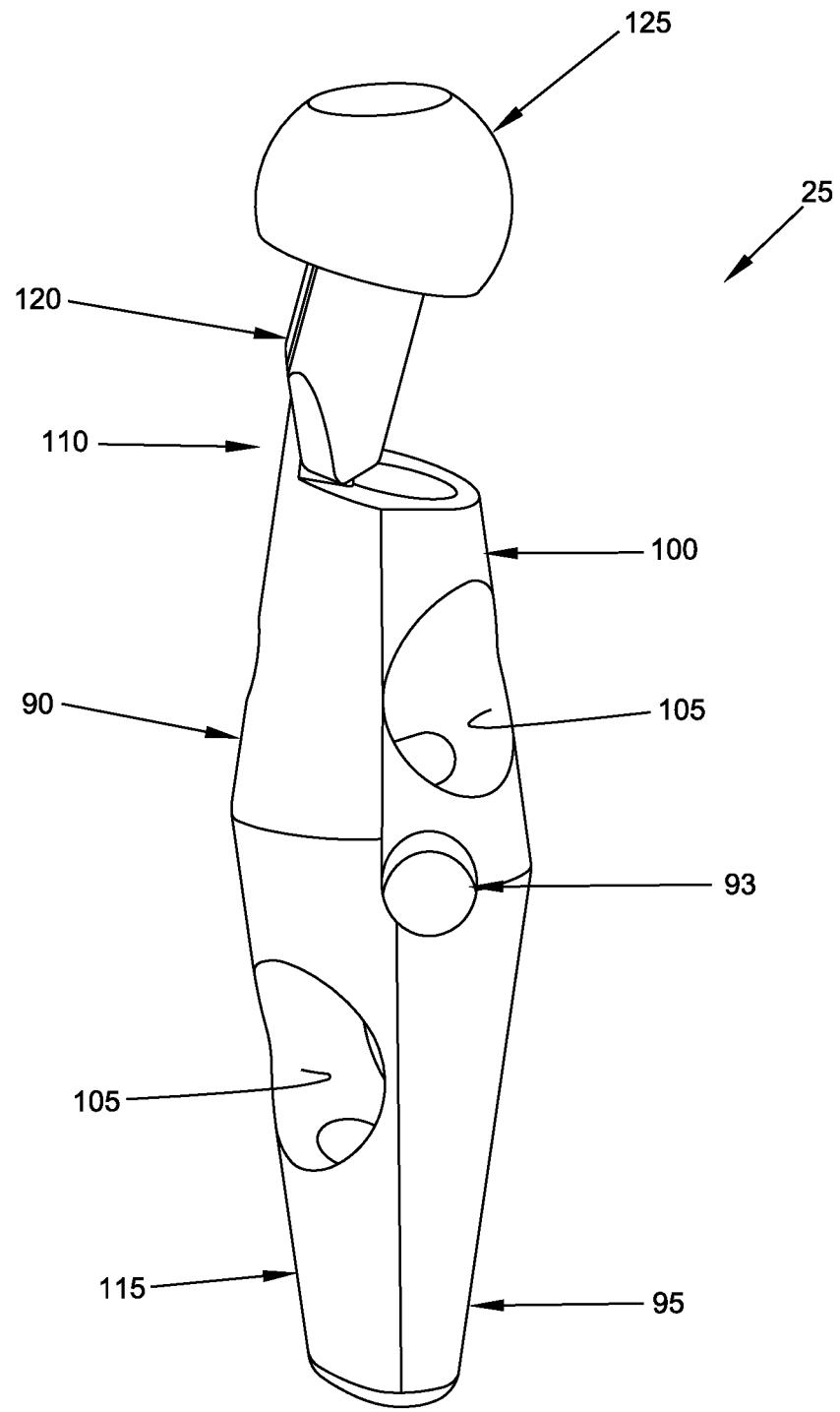
Figure 12:
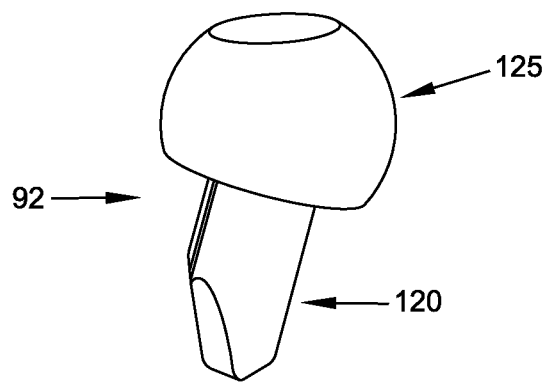
FIGS. 12-14 are schematic views showing further details of the pivoting component of FIGS. 6-11.
Figure 13:
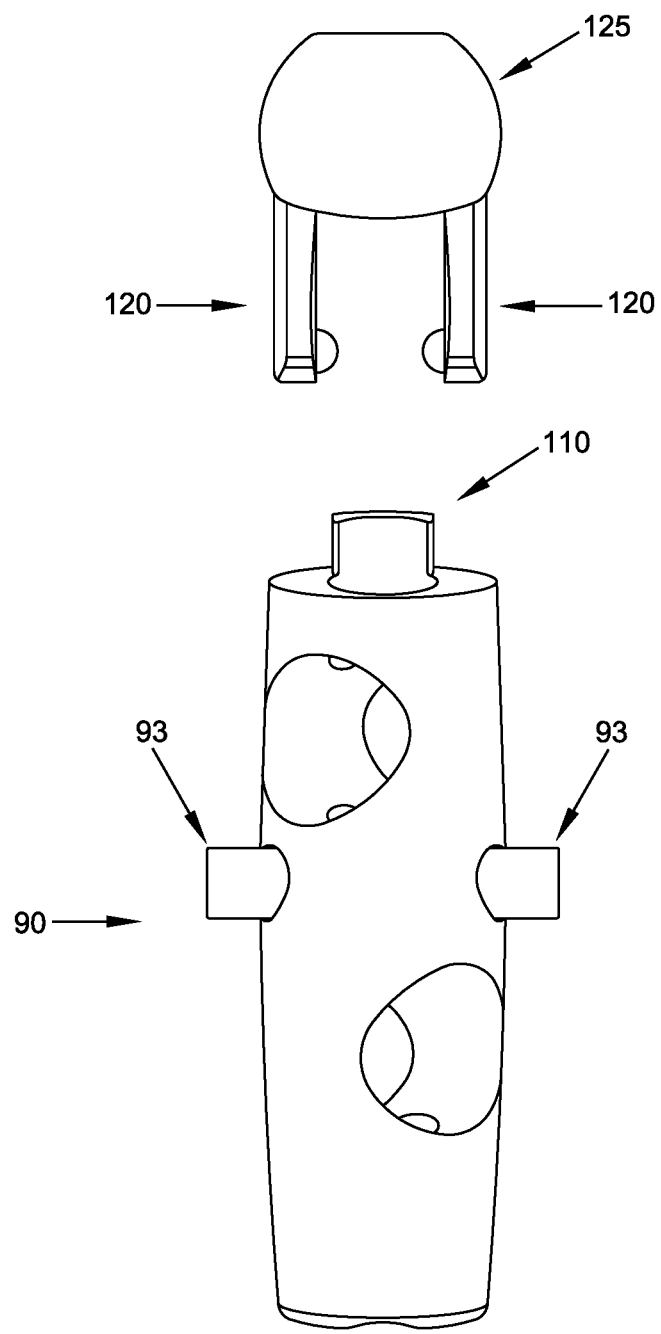
Figure 14:
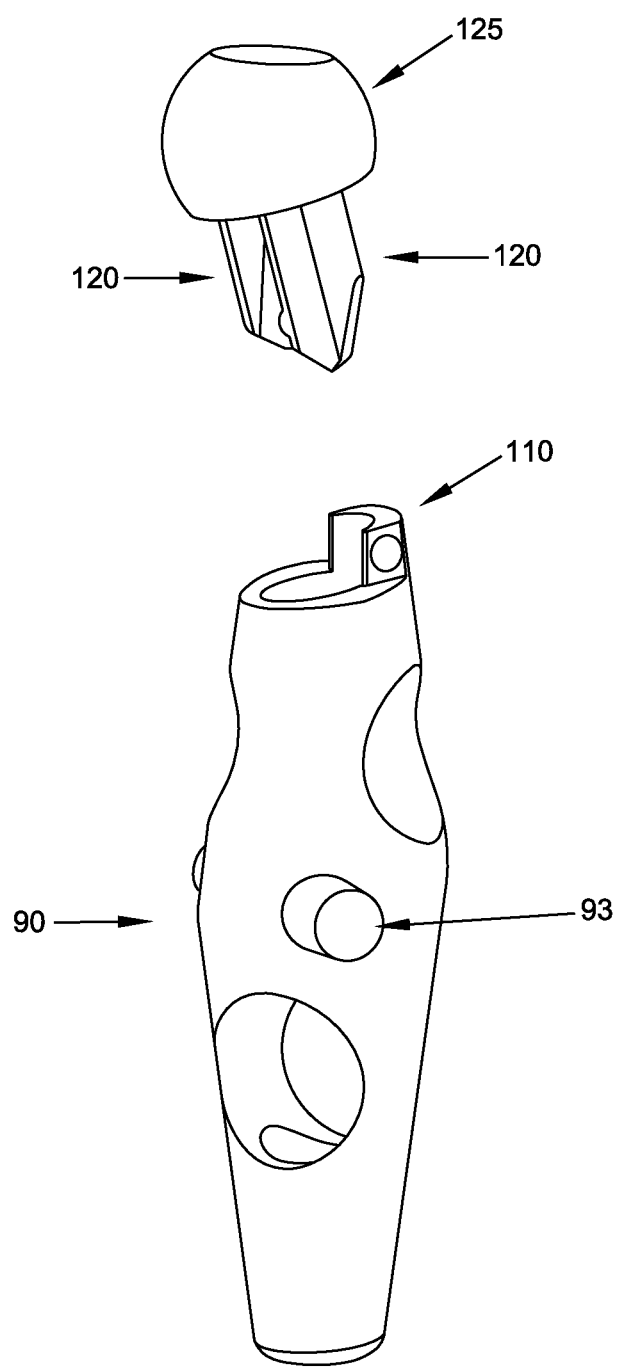

Looking next at FIGS. 4-6, intramedullary rod 10 generally comprises a tube 30 having a distal section 35, a proximal section 40, and a lumen 45 extending therebetween and opening on the proximal end of tube 30. In one preferred form of the present invention, lumen 45 comprises an internal screw thread 46 formed along the inner surface of lumen 45, along proximal section 40 of tube 30, for receiving an adjustment screw 50 and a set screw 55 as will hereinafter be discussed in greater detail.

Distal section 35 comprises at least one static distal seat 60 (FIG. 6) formed in distal section 35 of tube 30 for receiving a distal interlocking screw 15 as the distal interlocking screw passes through a first (e.g., lateral) portion of the distal bone fragment 7 and into a second (e.g., medial) portion of the distal bone fragment 7, the at least one static distal seat 60 comprising a round opening 65 on a first (e.g., lateral) side of tube 30 and a round opening 70 on a second (e.g., medial) side of tube 30, the round openings 65, 70 being disposed on an axis which extends substantially perpendicular to the longitudinal axis of tube 30 and being sized so as to form a snug interference fit with a distal interlocking screw 15 therein.

Proximal section 40 comprises at least one dynamic proximal seat 75 (FIG. 6) formed in proximal section 40 of tube 30 for receiving a proximal interlocking screw 20 as the proximal interlocking screw passes through a first (e.g., anterolateral) portion of the proximal bone fragment and into a second (e.g., posteromedial) portion of the proximal bone fragment, the at least one dynamic proximal seat 75 comprising an oblong opening 80 on the first (e.g., anterolateral) side of tube 30 and an oblong opening 85 on the second (e.g., posteromedial) side of tube 30, the oblong openings 80, 85 being disposed on an axis which extends substantially perpendicular to the longitudinal axis of the tube 30, the oblong openings 80, 85 being sized so as to form a loose interference fit with a proximal interlocking screw 20 therein, and the oblong openings 80, 85 being in alignment with openings formed in pivoting component 25, as will hereinafter be discussed in greater detail.

Looking next at FIGS. 3-14, pivoting component 25 comprises a body 90 and an adjuster 92. Body 90 is pivotally mounted within tube 30 of intramedullary rod 10 (e.g., via pivot pins 93), and has a distal end 95, a proximal end 100, and one or more round openings 105 passing through body 90, round openings 105 being aligned substantially perpendicular to the longitudinal axis of body 90 and in lateral alignment with oblong openings 80, 85 formed in tube 30 such that a proximal interlocking screw 20 may pass through an oblong opening 80 in tube 30, through a round opening 105 and through an oblong opening 85 on the opposite side of tube 30 (see FIG. 5). It should be appreciated that pivoting component 25, a round opening 105 and a pair of laterally aligned oblong openings 80, 85 in proximal section 40 of tube 30 together constitute the dynamic proximal seat 75 discussed above. Importantly, a proximal interlocking screw 20 which is passed through oblong opening 80, through round opening 105 and through another oblong opening 85 makes a snug interference fit with round opening 105 of body 90 of pivoting component 25 and a loose interference fit with oblong openings 80, 85 of proximal section 40 of tube 30, such that pivoting component 25 can move proximal interlocking screw 20 (and hence proximal bone fragment 8) when pivoting component 25 pivots within tube 30 of intramedullary rod 10, as will hereinafter be discussed in greater detail.

In one preferred form of the present invention, pivoting component 25 is pivotally mounted intermediate distal section 35 and proximal section 40 of tube 30 (e.g., via pivot pins 93) such that pivoting component 25 can pivot within lumen 45 relative to the longitudinal axis of tube 30 on an axis intermediate distal end 95 and proximal end 100 of body 90. In a preferred form of the present invention, pivoting component 25 comprises a finger 110 at its proximal end and a tapered distal section 115 at its distal end (FIGS. 7-14).

Adjuster 92 links adjustment screw 50 to body 90 of pivoting component 25, and comprises a pair of mounts 120 and a globular element 125. Mounts 120 pivotally connect to finger 110 of body 90, and globular element 125 is slidably received within adjustment screw 50 which is, in turn, threadingly engaged in the threaded proximal portion 46 of tube 30. The pivoting interaction of mounts 120 of adjuster 92 with finger 110 of body 90 are configured to translate longitudinal movement of adjustment screw 50 (which contacts globular element 125 of adjuster 92) into pivoting movement of finger 120 within tube 30, and hence pivoting movement of body 90 of pivoting component 25 within tube 30.

Figure 15:
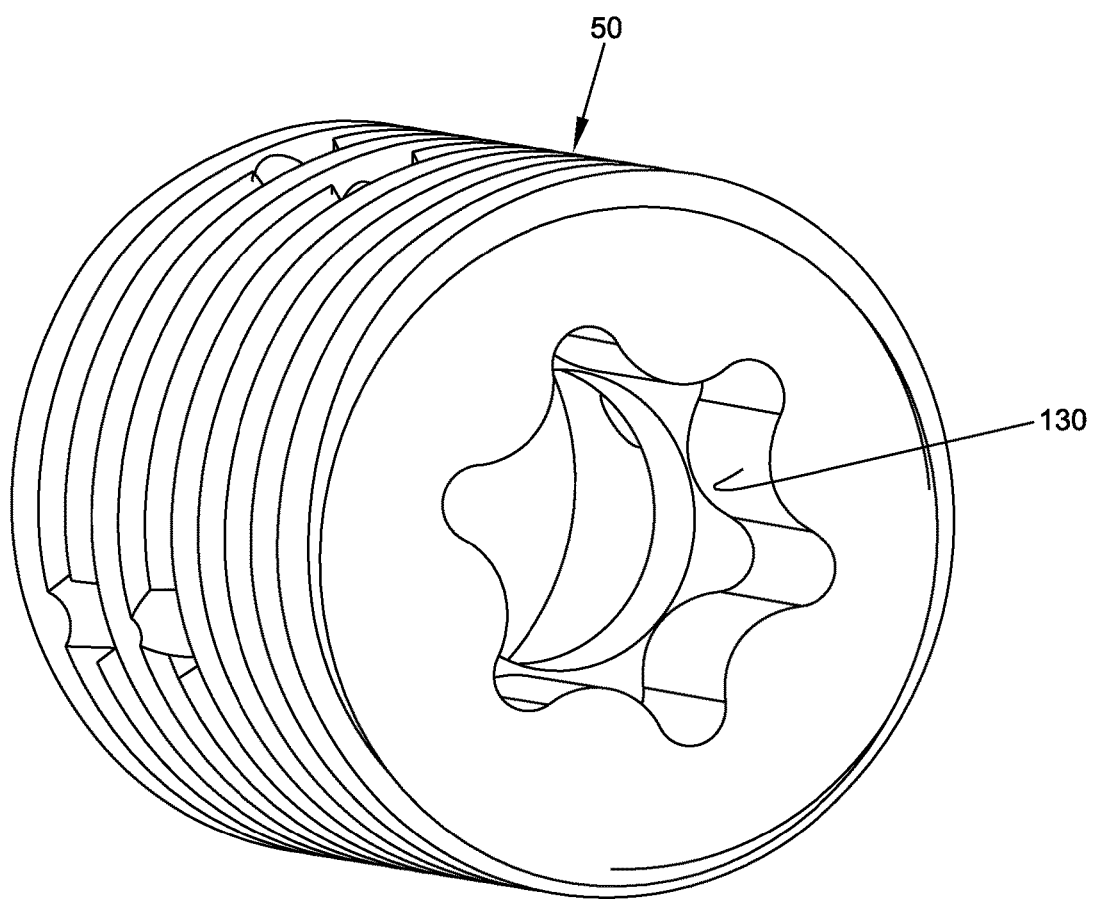
FIGS. 15 and 16 are schematic views showing further details of the adjustment screw of FIGS. 6-11.
Figure 16:
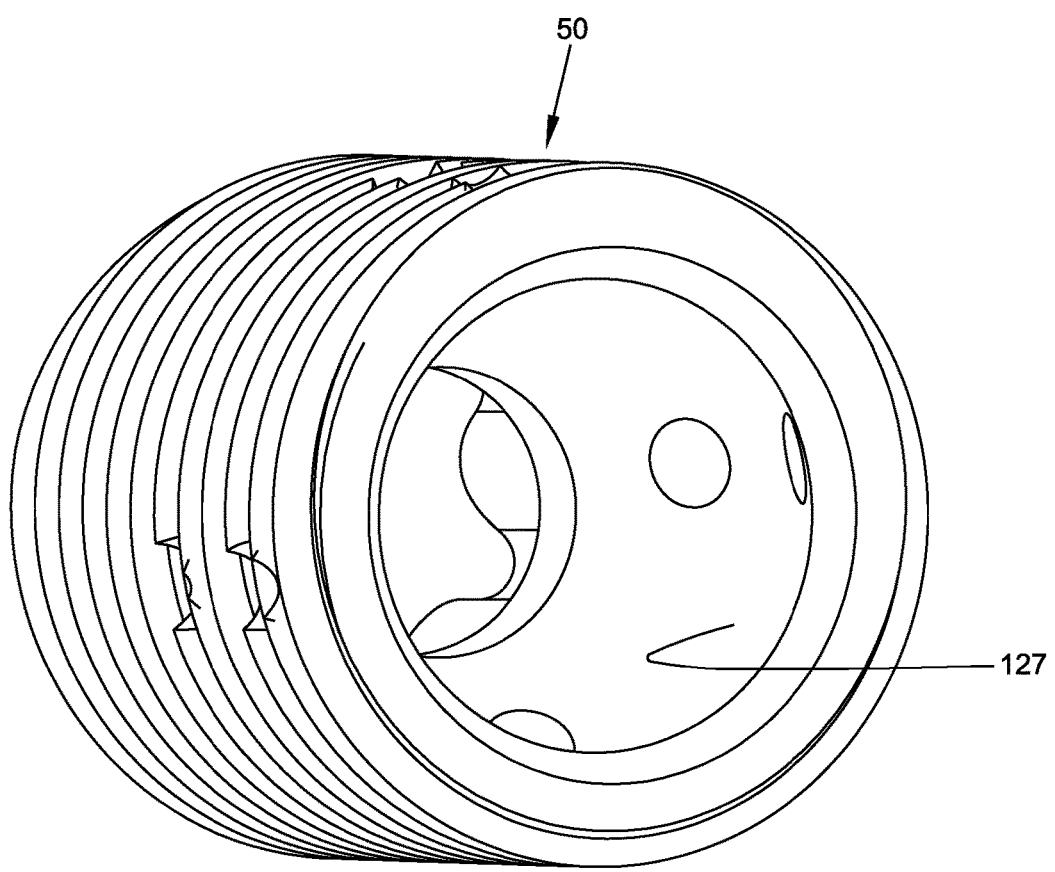

Looking next at FIGS. 15 and 16, in one preferred form of the present invention, adjustment screw 50 comprises a threaded screw having a cavity 127 for receiving globular element 125 therein and a hexaglobular opening 130 for selective engagement by a driver D (FIGS. 1-4 and 18-20). Adjustment screw 50 is threadingly mounted within the threaded proximal portion 46 of tube 30 such that rotation of adjustment screw 50 (i.e., via driver D) causes longitudinal movement of adjustment screw 50 within tube 30, and hence pivoting movement of finger 120 within tube 30, and hence pivoting movement of body 90 of pivoting component 25 within tube 30. As a result, when one or more proximal interlocking screw(s) 20 are disposed in dynamic proximal seat 75 (and hence disposed within the proximal bone fragment 8, tube 30 and body 90 of pivoting component 25), longitudinal motion of adjustment screw 50 will cause pivoting motion of body 90 of pivoting component 25 and hence pivoting motion of proximal bone fragment 8 relative to distal bone fragment 7 along the line of the fracture 9.

Figure 17:
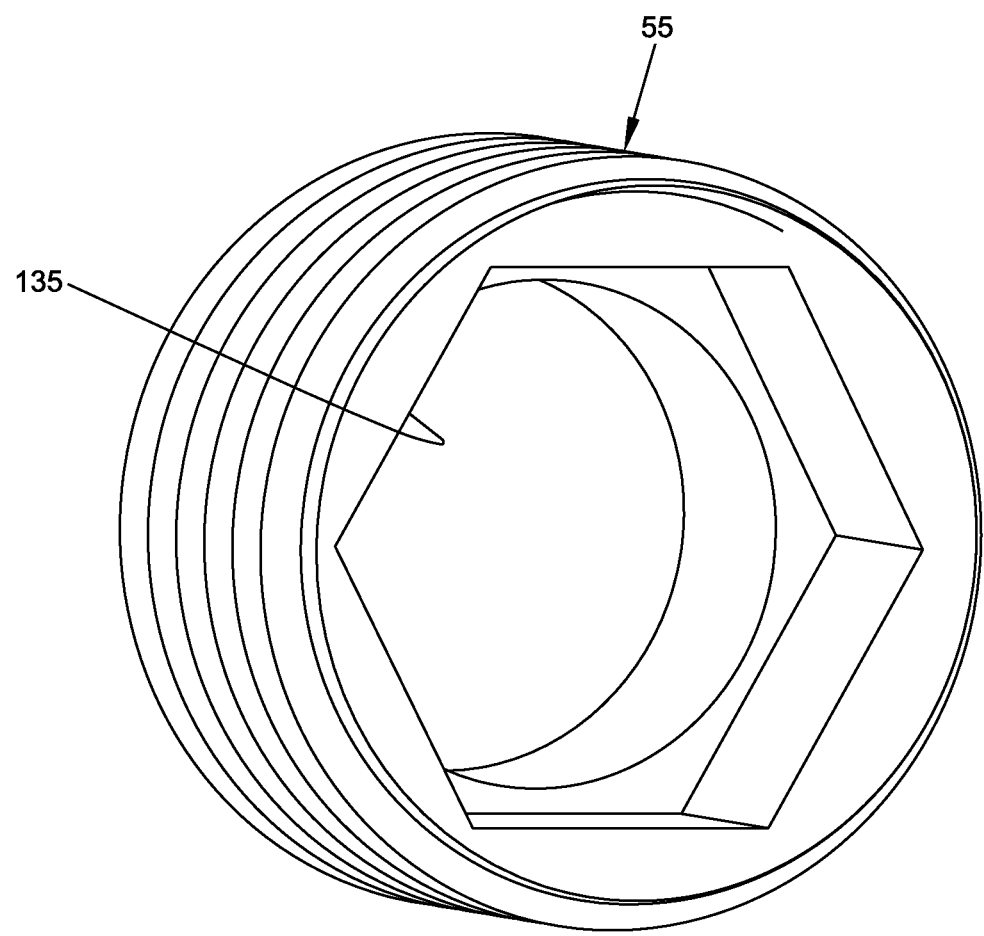
FIG. 17 is a schematic view showing further detail of the set screw of FIGS. 6-11.
Figure 18:
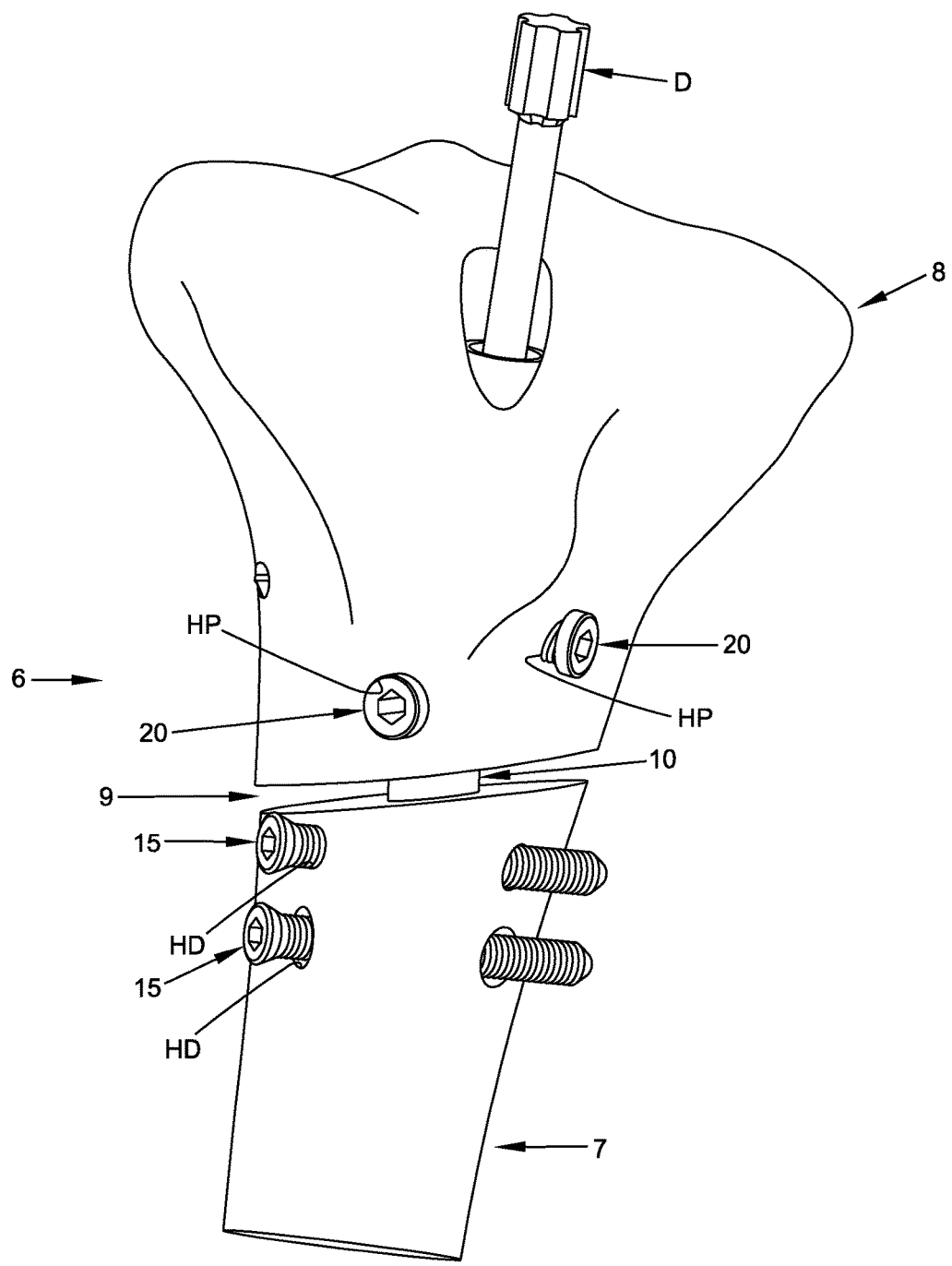
FIGS. 18 and 19 are schematic views showing the novel interlocking intramedullary rod assembly of FIG. 1 disposed in the proximal tibia with the interlocking intramedullary rod assembly spanning a fracture line, such that a distal bone fragment and a proximal bone fragment are mounted to the interlocking intramedullary rod assembly by lag screws.
Figure 19:
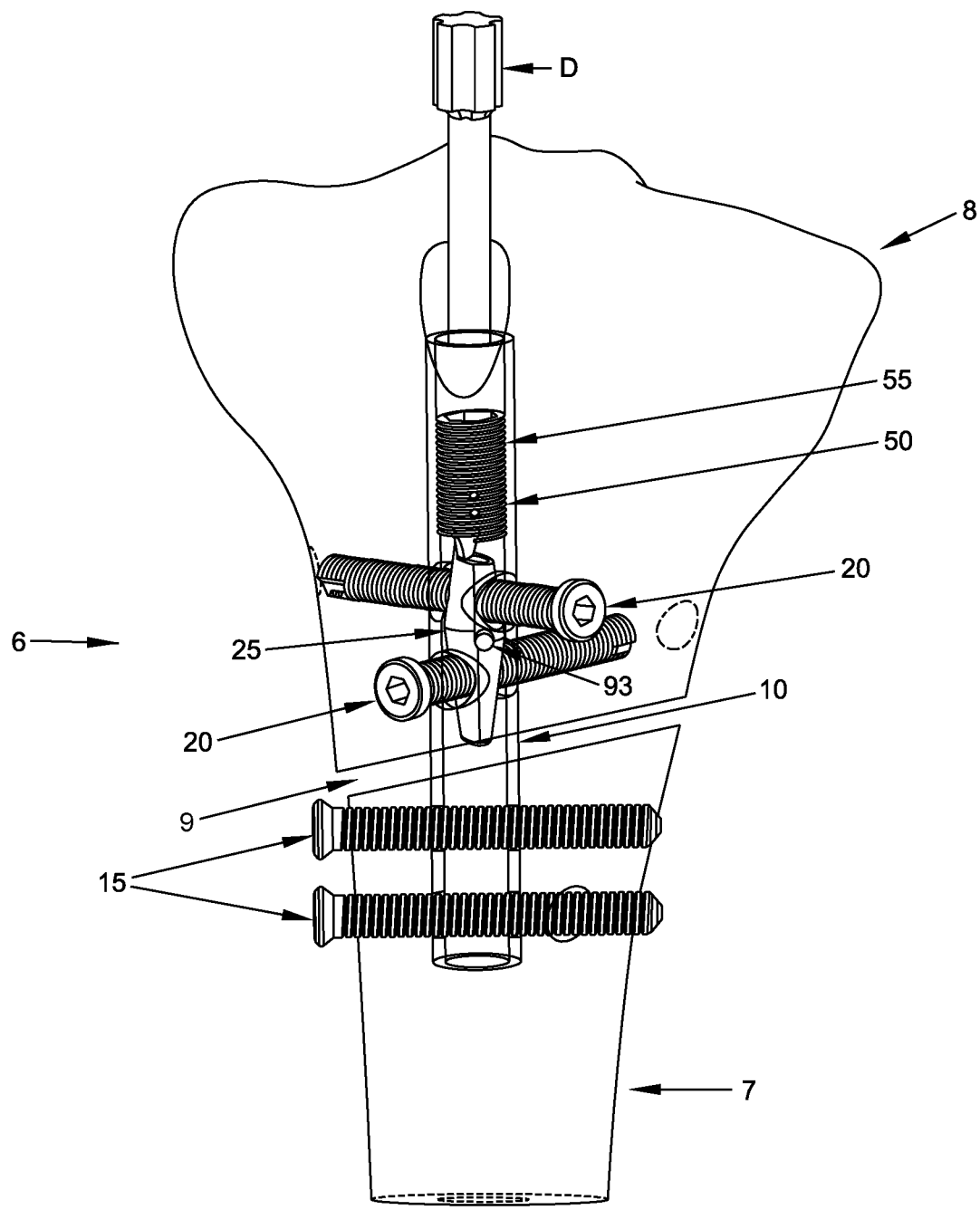
Figure 20:
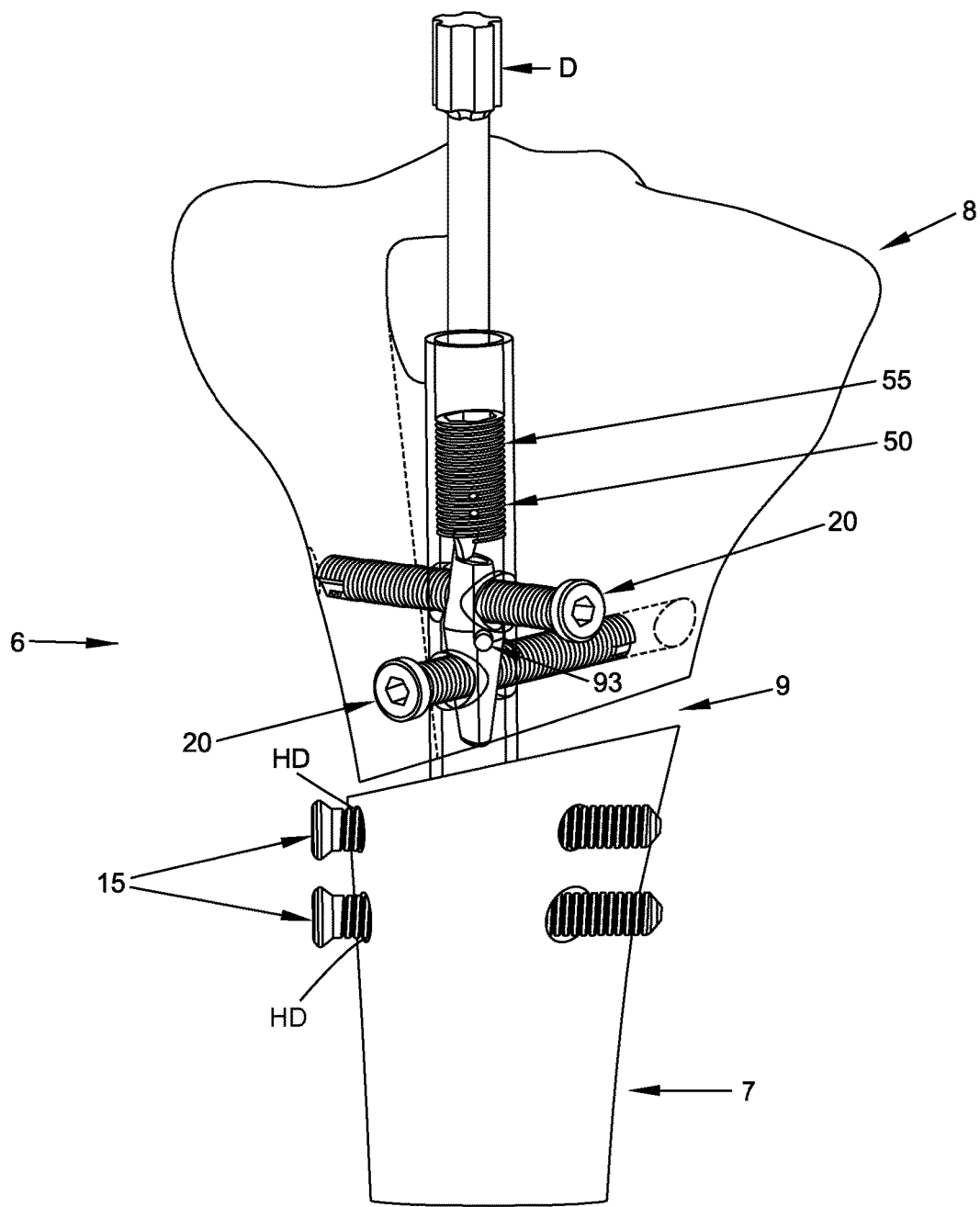
FIGS. 20-23 are schematic views showing the novel interlocking intramedullary rod assembly of FIG. 1 disposed in the proximal tibia with the interlocking intramedullary rod assembly spanning a fracture line, and with a driver being used to selectively pivot the proximal bone fragment relative to the distal bone fragment across the fracture line so as to reduce a fracture in the proximal tibia and so as to allow the surgeon to precisely align the proximal bone fragment relative to the distal bone fragment in order to facilitate healing of the fracture.
Figure 21:
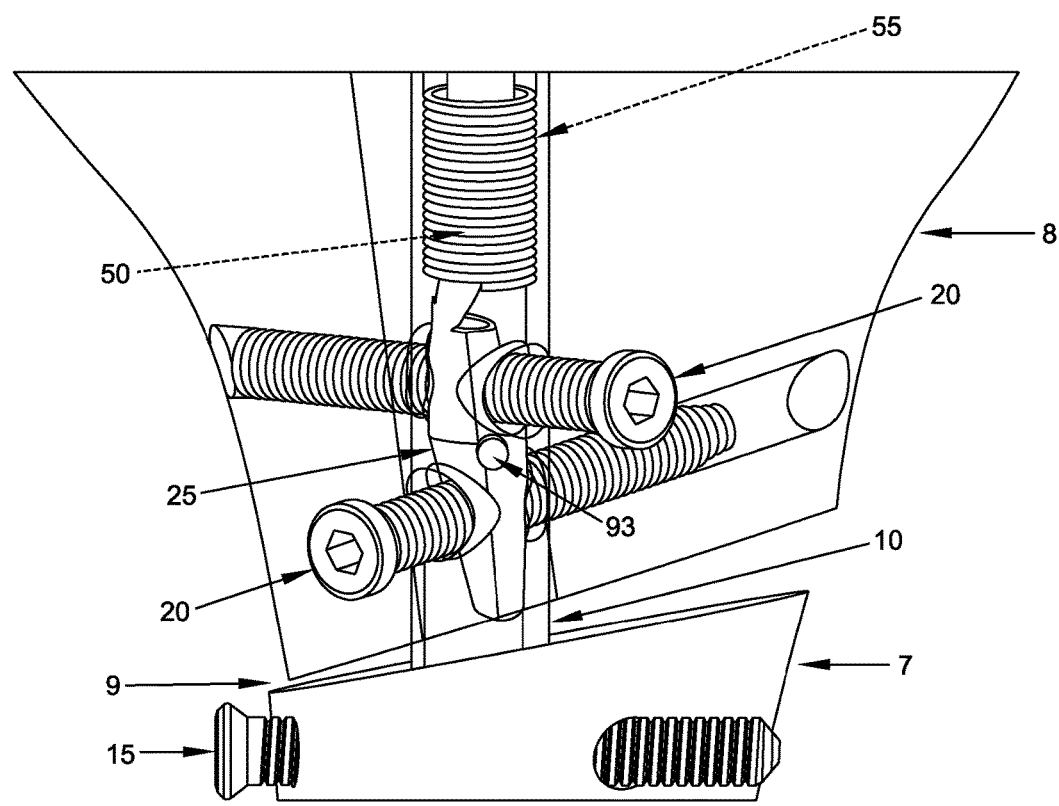
Figure 22:
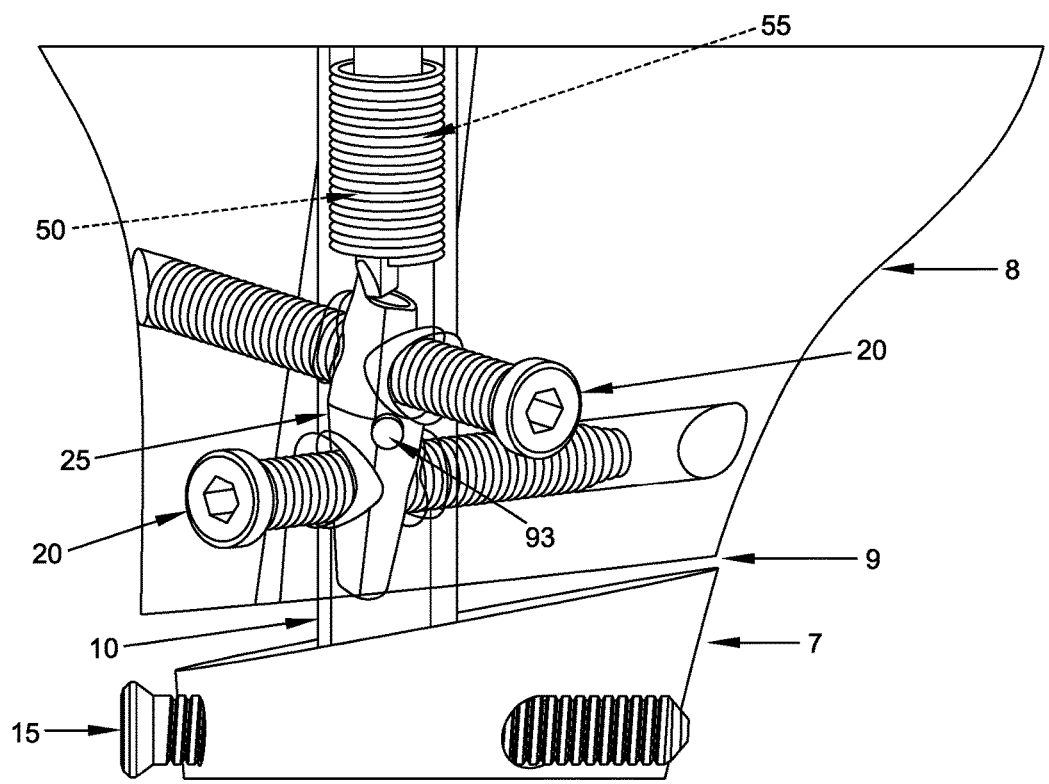
Figure 23:
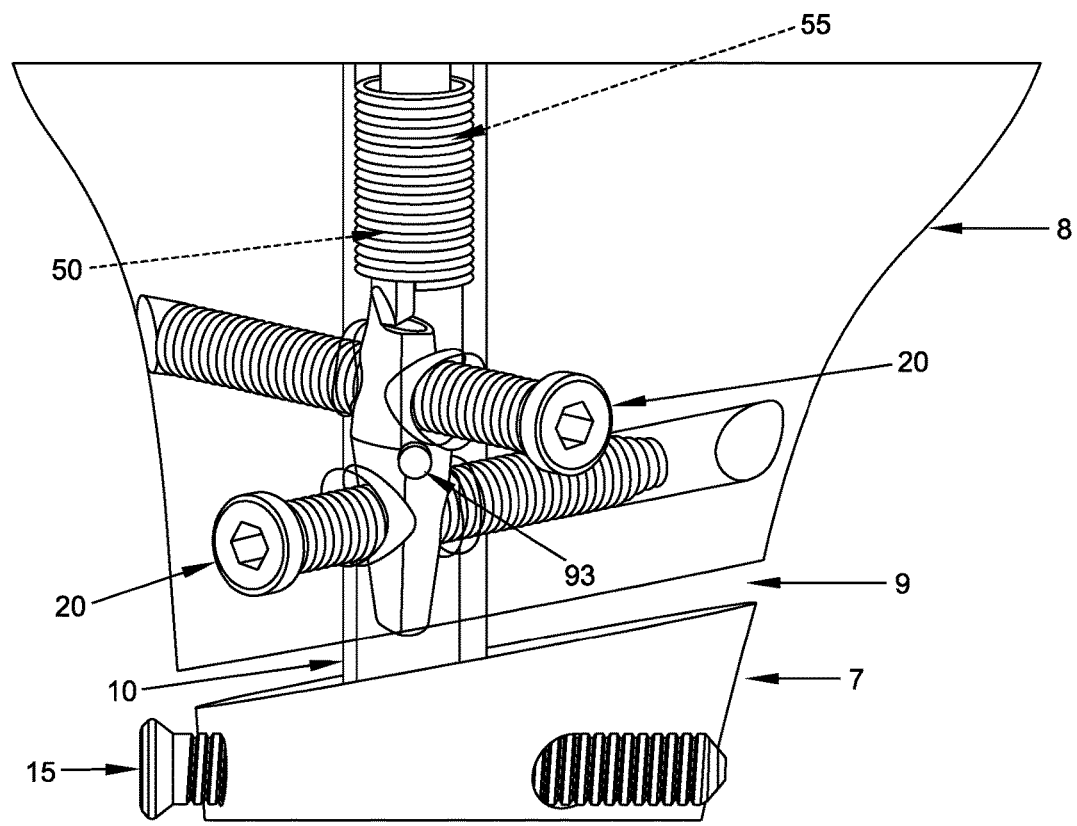

Looking next at FIG. 17, in one preferred form of the present invention, set screw 55 comprises a hexagonal opening 135 for engagement by a driver (e.g., driver D, or another driver). Set screw 55 is threadingly mounted within the threaded proximal portion of tube 30 such that the set screw can be advanced distally (i.e., by rotating the set screw). In use, when proximal bone fragment 8 has been selectively pivoted into the desired position vis-à-vis distal bone fragment 7 (i.e., by rotating adjustment screw 50, which in turn pivots pivoting component 25 and hence moves the at least one proximal interlocking screw 20), a driver (e.g., diver D, or another driver) may be used to advance set screw 55 distally such that set screw 55 engages adjustment screw 50 and prevents further longitudinal movement of the adjustment screw. As a result, when set screw 55 engages adjustment screw 50, adjuster 92 (and hence pivoting component 25) are locked in position, whereby to prevent further pivoting of proximal bone fragment 8 relative to distal bone fragment 7.

Method of Treating a Tibial Fracture use, and looking now at FIGS. 18-23, novel interlocking intramedullary rod assembly 5 may be used to treat a fracture of the tibia in the following manner.

First, the surgeon creates an opening within the intramedullary canal of the tibia in order to receive intramedullary rod 10 of interlocking intramedullary rod assembly 5 (e.g., by reaming the intramedullary canal of the tibia). It should be noted that the portion of the intramedullary canal which passes through proximal bone fragment 8 should be reamed to a larger degree than the portion of the intramedullary canal which passes through distal bone fragment 7, such that some movement is permitted between proximal bone fragment 8 and intramedullary rod 10 (i.e., as proximal bone fragment 8 pivots relative to intramedullary rod 10). Alternatively, where the intramedullary canal is "spongy", the reaming of the portion of the intramedullary canal passing through proximal bone fragment 8 does not need to be larger than the diameter of intramedullary rod 10 disposed in proximal bone fragment 8, inasmuch as the "spongy" nature of the intramedullary canal permits proximal bone fragment 8 to pivot relative to intramedullary rod 10).

The surgeon then inserts intramedullary rod 10 (i.e., tube 30) into the opening formed in the bone.

Next, the surgeon drills one or more holes HD in distal bone fragment 7, the one or more holes HD passing through both the lateral and medial portions of the distal bone fragment 7 perpendicular to tube 30, with each hole HD being aligned with a static distal seat 60 formed in the distal section 35 of tube 30. The surgeon then passes a distal interlocking screw 15 through a hole HD formed in the distal bone fragment and through a static distal seat 60. Note that distal interlocking screw 15 forms a snug interference fit with tube 30, whereby to form a snug connection between distal bone fragment 7 and intramedullary rod 10.

Using an aimer/jig, the surgeon next drills one or more holes HP through both the lateral and medial portions of proximal bone fragment 8, the one or more holes HP being aligned substantially perpendicular to tube 30, with each hole HP being aligned with a dynamic proximal seat 75. The surgeon then passes a proximal interlocking screw 20 through a hole HP formed in the proximal bone fragment and through a dynamic proximal seat 75, such that the proximal interlocking screw 20 passes through a pair of oblong openings 80, 85 formed in tube 30 and through a round opening 105 in body 90 of pivoting component 25. Note that proximal interlocking screw 20 forms a loose fit with tube 30 and a snug interference fit with body 90 of pivoting component 25, whereby to form an adjustable connection between proximal bone fragment 8 and intramedullary rod 10.

At this point in the procedure, distal bone fragment 7 has been secured to intramedullary rod 10 and proximal bone fragment 8 has been secured to body 90 of pivoting component 25 (which is in turn pivotally connected to intramedullary rod 10), with tube 30 of intramedullary rod 10 spanning fracture line 9 in the tibia.

Next, the surgeon uses a hexaglobular driver (e.g., driver D) to selectively rotate adjustment screw 50 within tube 30, whereby to selectively move adjustment screw 50 longitudinally within tube 30, and hence to selectively pivot body 90 of pivoting component 25 within tube 30, and thereby selectively pivot proximal bone fragment 8 (which is connected to pivoting component 25 via one or more proximal interlocking screws 20). As a result, the surgeon can use a driver to longitudinally move adjustment screw 50 within tube 30 and pivot body 90 of pivoting component 25 within tube 30, thereby allowing the surgeon to selectively adjust the disposition of proximal bone fragment 8 relative to the disposition of distal bone fragment 7 at the fracture line 9. It should also be appreciated that by allowing the surgeon to selectively adjust the disposition of proximal bone fragment 7 about the proximal end of intramedullary rod 10, the present invention not only allows the surgeon to manipulate the angular disposition of proximal bone fragment 8 relative to distal bone fragment 7, but also allows the surgeon to tailor the degree of angular compression established between proximal bone fragment 8 and distal bone fragment 7 at fracture line 9, e.g., by pivoting proximal bone fragment 8 relative to distal bone fragment 7 so as to apply a desired degree of angular compression to the medial side of the bone, the lateral side of bone, etc. When the desired angle of disposition has been achieved, the surgeon removes the hexaglobular driver and uses a hex driver (e.g., driver D or another driver) to rotate set screw 55, whereby to lock adjustment screw 50 into position, whereby to lock pivoting component 25 into position, and hence to lock proximal bone fragment 8 relative to distal bone fragment 7.

Figure 24:
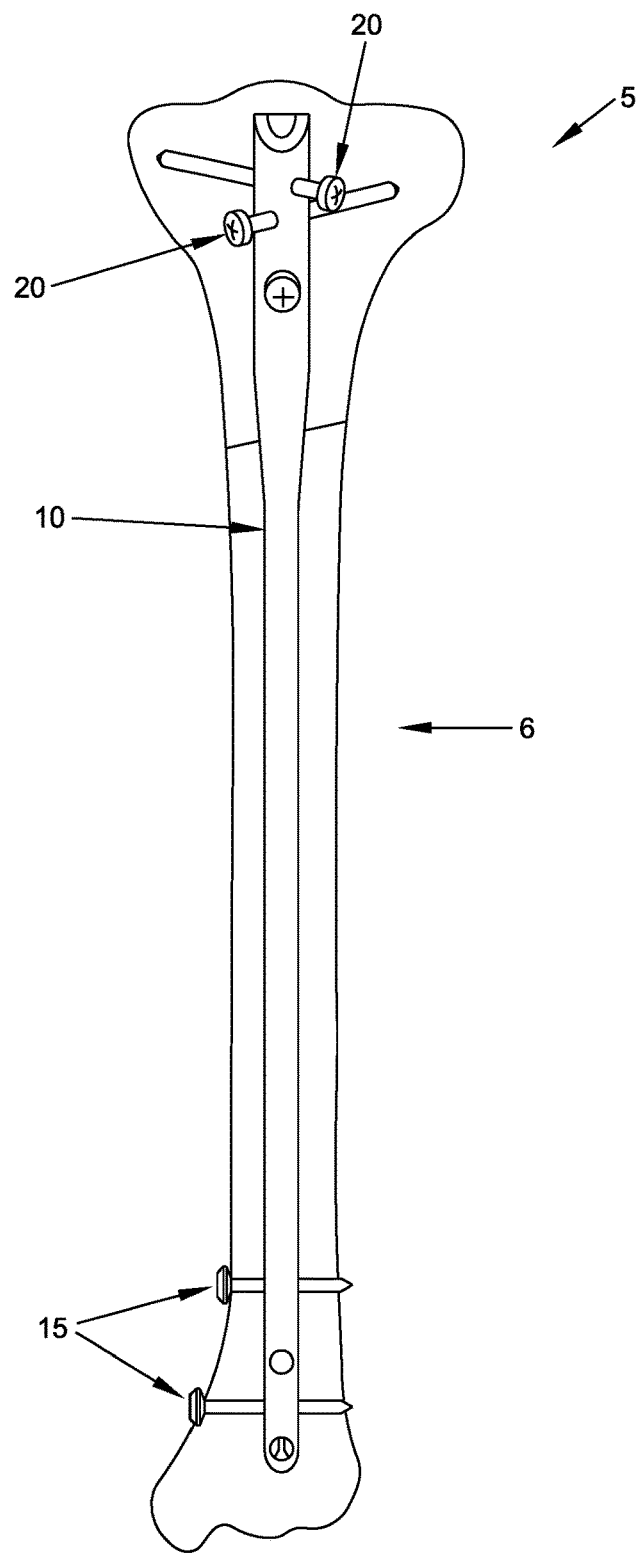
FIG. 24 is a schematic view showing another configuration of the novel interlocking intramedullary rod assembly of the present invention.

For ease of illustration, novel interlocking intramedullary rod assembly 5 has been shown in FIGS. 1-3 and 18-23 disposed in the proximal portion of a bone (e.g., the tibia), with intramedullary rod 10 having a relatively short length and distal interlocking screws 15 being disposed relatively close to fracture line 9. However, it should be appreciated that in many applications (e.g., in long bones such as the tibia), it may be desirable for intramedullary rod 10 to have a relatively long length and for distal interlocking screws 15 to be set fairly far from fracture line 9. See, for example, FIG. 24, which shows an interlocking intramedullary rod assembly 5 having a relatively long intramedullary rod 10 and having distal interlocking screws 15 disposed relatively far from a fracture line 9.

In addition to the foregoing, although novel interlocking intramedullary rod assembly 5 has been described and shown above as being inserted into a bone in a proximal-to-distal manner, with the proximal bone fragment being pivotable relative to the distal bone fragment, it should also be appreciated that, if desired, novel interlocking intramedullary rod assembly 5 may, alternatively, be inserted into the bone in a distal-to-proximal manner. When novel interlocking intramedullary rod assembly 5 is used in this manner, the distal bone fragment is pivotable relative to the proximal bone fragment (where the terms "distal" and "proximal" relate the frame of reference of the patient's limb).

And it should also be appreciated that the present invention may be used to facilitate healing of a fracture in substantially any bone where it is desirable to pivot one bone fragment relative to another bone fragment and fix the fragments in position to facilitate healing. By way of example but not limitation, such bone could include the tibia, the femur, the humerus, etc.

Modifications of the Preferred Embodiments

Although the present invention has been described herein with reference to particular embodiments, it is to be understood that these embodiments are merely illustrative of the principles and applications of the present invention. It is, therefore, to be understood that numerous modifications may be made to the illustrative embodiments and that other arrangements may be devised without departing from the spirit and scope of the present invention.

What is claimed is:

1. An interlocking intramedullary rod assembly for treating a fracture of a bone, said interlocking intramedullary rod assembly comprising:

an intramedullary rod comprising a distal section, a proximal section, a longitudinal axis extending between said distal section and said proximal section, and a lumen opening on said proximal section;

a pivoting component comprising at least two bores passing therethrough, said pivoting component being pivotally disposed in said lumen of said intramedullary rod, said pivoting component being selectively pivotable relative to said longitudinal axis of said intramedullary rod;

an adjustment screw disposed in said proximal section of said intramedullary rod, said adjustment screw being aligned with said longitudinal axis of said intramedullary rod;

a distal interlocking screw comprising a distal end and a proximal end; and a proximal interlocking screw comprising a distal end and a proximal end;

wherein said at least two bores of said pivoting component are sized and configured to receive said proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod and to said pivoting component such that said proximal interlocking screw passes through one of said at least two bores formed in said pivoting component, and such that said proximal interlocking screw can be selectively pivoted relative to said longitudinal axis of said intramedullary rod by selectively pivoting said pivoting component; and wherein rotation of said adjustment screw causes longitudinal movement of said adjustment screw along said longitudinal axis of said intramedullary rod, and further wherein longitudinal movement of said adjustment screw along said longitudinal axis of said intramedullary rod causes said pivoting component to pivot relative to said longitudinal axis of said intramedullary rod, whereby to selectively pivot said proximal interlocking screw relative to said longitudinal axis of said intramedullary rod.

2. An interlocking intramedullary rod assembly according to claim 1 further comprising a set screw disposed in said proximal section of said intramedullary rod, wherein rotation of said set screw prevents rotation of said adjustment screw, whereby to selectively lock said pivoting component and said proximal interlocking screw in position.

3. An interlocking intramedullary rod assembly according to claim 1 wherein said static distal seat comprises a first round opening and a second round opening.

4. An interlocking intramedullary rod assembly according to claim 3 wherein said first round opening is disposed on a first side of said intramedullary rod and said second round opening is disposed on a second side of said intramedullary rod.

5. An interlocking intramedullary rod assembly according to claim 4 wherein said first round opening is aligned with said second round opening along an axis which extends substantially perpendicular to said longitudinal axis of said intramedullary rod.

6. An interlocking intramedullary rod assembly according to claim 3 wherein said distal interlocking screw comprises a shaft sized to make a tight fit within said first round opening and said second round opening.

7. An interlocking intramedullary rod assembly according to claim 1 wherein said dynamic proximal seat comprises a first oblong opening in said intramedullary rod, a second oblong opening in said intramedullary rod, and a round hole in said pivoting component.

8. An interlocking intramedullary rod assembly according to claim 7 wherein said first oblong opening, said second oblong opening, and said round hole are disposed on an axis which extends substantially perpendicular to said longitudinal axis of said intramedullary rod.

9. An interlocking intramedullary rod assembly according to claim 8 wherein said proximal interlocking screw comprises a shaft sized to make a tight fit within said round hole of said pivoting component and a loose fit with said first oblong opening and said second oblong opening.

10. An interlocking intramedullary rod assembly for treating a fracture of a bone, said interlocking intramedullary rod assembly comprising:

an intramedullary rod comprising a distal section, a proximal section, a longitudinal axis extending between said distal section and said proximal section, and a lumen opening on said proximal section;

a pivoting component comprising a bore passing therethrough, said pivoting component being pivotally disposed in said lumen of said intramedullary rod, said pivoting component being selectively pivotable relative to said longitudinal axis of said intramedullary rod;

an adjustment screw disposed in said proximal section of said intramedullary rod, said adjustment screw being aligned with said longitudinal axis of said intramedullary rod;

a distal interlocking screw comprising a distal end and a proximal end; and a proximal interlocking screw comprising a distal end and a proximal end;

wherein said bore of said pivoting component is sized and configured to receive said proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod and to said pivoting component such that said proximal interlocking screw passes through said bore formed in said pivoting component, and such that said proximal interlocking screw can be selectively pivoted relative to said longitudinal axis of said intramedullary rod by selectively pivoting said pivoting component; and wherein rotation of said adjustment screw causes longitudinal movement of said adjustment screw along said longitudinal axis of said intramedullary rod, and further wherein longitudinal movement of said adjustment screw along said longitudinal axis of said intramedullary rod causes said pivoting component to pivot relative to said longitudinal axis of said intramedullary rod, whereby to selectively pivot said proximal interlocking screw relative to said longitudinal axis of said intramedullary rod.

11. An interlocking intramedullary rod assembly according to claim 10 further comprising a set screw disposed in said proximal section of said intramedullary rod, wherein rotation of said set screw prevents rotation of said adjustment screw, whereby to selectively lock said pivoting component and said proximal interlocking screw in position.

12. An interlocking intramedullary rod assembly according to claim 10 wherein said static distal seat comprises a first round opening and a second round opening.

13. An interlocking intramedullary rod assembly according to claim 12 wherein said first round opening is disposed on a first side of said intramedullary rod and said second round opening is disposed on a second side of said intramedullary rod.

14. An interlocking intramedullary rod assembly according to claim 13 wherein said first round opening is aligned with said second round opening along an axis which extends substantially perpendicular to said longitudinal axis of said intramedullary rod.

15. An interlocking intramedullary rod assembly according to claim 12 wherein said distal interlocking screw comprises a shaft sized to make a tight fit within said first round opening and said second round opening.

16. An interlocking intramedullary rod assembly according to claim 10 wherein said dynamic proximal seat comprises a first oblong opening in said intramedullary rod, a second oblong opening in said intramedullary rod, and a round hole in said pivoting component.

17. An interlocking intramedullary rod assembly according to claim 16 wherein said first oblong opening, said second oblong opening, and said round hole are disposed on an axis which extends substantially perpendicular to said longitudinal axis of said intramedullary rod.

18. An interlocking intramedullary rod assembly according to claim 17 wherein said proximal interlocking screw comprises a shaft sized to make a tight fit within said round hole of said pivoting component and a loose fit with said first oblong opening and said second oblong opening.

* * * * *